(12) United States Patent
Friedland

(10) Patent No.: US 7,524,661 B2
(45) Date of Patent: Apr. 28, 2009

(54) PREPARATION OF A THERAPEUTIC COMPOSITION

(75) Inventor: Bernard Friedland, Sarasota, FL (US)

(73) Assignee: Advanced Viral Research Corporation, Yonkers, NY (US)

(*) Notice: Subject to any disclaimer, the term of this patent is extended or adjusted under 35 U.S.C. 154(b) by 0 days.

(21) Appl. No.: 11/346,146

(22) Filed: Feb. 1, 2006

(65) Prior Publication Data

US 2006/0177514 A1    Aug. 10, 2006

Related U.S. Application Data

(60) Continuation of application No. 10/201,206, filed on Jul. 22, 2002, now Pat. No. 7,074,767, which is a division of application No. 09/764,017, filed on Jan. 17, 2001, now Pat. No. 6,528,098, which is a continuation-in-part of application No. 09/344,095, filed on Jun. 25, 1999, now Pat. No. 6,303,153, which is a continuation-in-part of application No. 08/735,236, filed on Oct. 22, 1996, now abandoned.

(51) Int. Cl.
    *C12P 1/06* (2006.01)
(52) U.S. Cl. ................ 435/169; 435/41; 435/68.1; 435/70.1; 435/71.1
(58) Field of Classification Search .............. 435/41, 435/68.1, 70.1, 71.1, 169
    See application file for complete search history.

(56) References Cited

U.S. PATENT DOCUMENTS

| 5,807,839 | A | | 9/1998 | Hirschman et al. |
| 5,807,840 | A | | 9/1998 | Hirschman et al. |
| 5,849,196 | A | * | 12/1998 | Kochel ............ 210/651 |
| 5,902,786 | A | | 5/1999 | Bregman et al. |

OTHER PUBLICATIONS

Lazzarino et al., Cytokine May 2001;14(4):234-9.*
Pihlanto-Leppala et al., "Biologically Active Peptides Derived Milk Proteins," Ch. 2, pp. 1-15 (2004).
Office Communication corresponding to an EP Application No. 00943141.2-1216 dated May 29, 2007.
English Translation of the Official Action corresponding to a CN Patent Application No. 200610003793.8 dated Aug. 3, 2007.
Official Action corresponding to a Canadian Patent Application No. 2,434,060 dated Sep. 14, 2007.
Chinese Office Action Corresponding to Chinese Patent Application for Invention No. 200610003793.8 dated May 23, 2008.

* cited by examiner

*Primary Examiner*—Ruth A Davis
(74) *Attorney, Agent, or Firm*—Jenkins, Wilson, Taylor & Hunt, P.A.

(57) ABSTRACT

Product R, a novel therapeutic composition for treating viral infections and stimulating the immune system, comprises a unique peptide having 31 amino acids and another unique peptide having 21 amino acids and connected with an oligonucleotide through a diphosphodiester or diphosphodithioate ester linkage. The composition has a light absorption spectrum with typical absorption ratios of 1.998 at 260 nm/280 nm and 1.359 at 260 nm/230 nm.

6 Claims, 23 Drawing Sheets

A-FRACTION A
T-TOTAL PRODUCT R
B-FRACTION B

PROTON NMR SPECTRUM OF PEPTIDE-A (IN $H_2O$)

CARBON/HYDROGEN HSQC SPECTRUM OF PEPTIDE-A

FIG.11 PROTON NMR SPECTRUM OF PEPTIDE-B

CARBON/HYDROGEN HSQC SPECTRUM OF PEPTIDE-B

STRUCTURE OF PEPTIDE-B

NATURE OF THE LINKAGE BETWEEN SERINE 18
AND DINUCLEOTIDE OF PEPTIDE-B

B1, B2 = CYTOSINE, GUANINE, ADENINE, THYMINE, URACIL, 5-METHYLCYTOSINE, 5-FLUOROURACIL
R1, R2 = H, OH
X = HYDROXYLATED AMINO-ACID RESIDUE
Y = PEPTIDE RESIDUES

MASS SPECTRAL DATA FOR PEPTIDE-B

SEQUENCE LISTING

<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Val Leu Pro Val Pro Gln Lys Ala Val Pro Tyr Pro Gln Arg Asp
 1               5                  10                  15

Met Pro Ile Gln Ala Phe Leu Leu Tyr Gln Glu Pro Val Leu Gly
             20                  25                  30

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Glu Ile Pro Asp Ala Gly Gly Arg Ile Val Asp Tyr Tyr Val Gly
 1               5                  10                  15

Phe Ser Asp Ser Val
             20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(21)
<223> OTHER INFORMATION: Residues could not be unambiguously
      determined in the sequence

<400> SEQUENCE: 3

Gly Glu Ile Pro Asp Ala Gly Gly Arg Ile Val Asp Tyr Tyr Val Gly
 1               5                  10                  15

Phe Ser Asp Xaa Xaa
             20

PREPARATION OF A THERAPEUTIC COMPOSITION

RELATED APPLICATIONS

This application is a continuation of application Ser. No. 10/201,206, filed on Jul. 22, 2002 now U.S. Pat. No. 7,074,767, which is a divisional of application Ser. No. 09/764,017, filed on Jan. 17, 2001, now U.S. Pat. No. 6,528,098, which is a continuation-in-part of application Ser. No. 09/344,095, filed on Jun. 25, 1999, now U.S. Pat. No. 6,303,153, which is a continuation-in-part of application Ser. No. 08/735,236, filed on Oct. 22, 1996, now abandoned, each of which is incorporated by reference herein in its entirety.

BACKGROUND OF THE INVENTION

1. Field of the Invention

The present invention relates to novel compounds having a structure comprising a polypeptide covalently bound to an oligo-nucleotide and useful as immune modulators for treating various viral infections and immune system diseases.

2. Description of the Related Art

The concept of an antiviral agent composed of peptones, peptides, proteins and nucleic acid was originated in 1934. After some years of experimentation, such an antiviral agent was modified by using bovine serum albumin in combination with peptone, and ribonucleic acid to produce an antiviral biotic agent which is nontoxic, free from anaphylactogenic properties and is miscible with tissue fluids and blood sera. The agent used to be described as a "lipopeptide-nucleic acid compound"[1] and registered under trademark RETICULOSE® by Chemico Laboratories, Inc. Physician Desk Reference, p 651, 1960. RETICULOSE® was reported as an antiviral agent for treating a variety of human viral infections, such as influenza, herpes, hepatitis A and B. It was then assumed that RETICULOSE® acts as an antiviral agent at least by increasing leukogenesis, synthesis of antibodies and enhancing phagocytosis. RETICULOSE® was last sold in the United States in 1964.

The method of making RETICULOSE® had been kept as a trade secret by the manufacture until the issuance of U.S. Pat. No. 5,849,196, which discloses the method of making RETICULOSE®.

As disclosed in U.S. Pat. No. 5,849,196, the starting materials for making RETICULOSE® consist of, by weight, 40-50% of casein, 1-10% of blood albumin, 15-40% of beef peptone, 10-25% of RNA and 5-25% of sodium hydroxide. These starting materials are suspended in water which yields a ratio of proteins (casein, peptone and blood albumin) to water equals to about 4.3 to about 100 by weight. After an autoclaving treatment of the mixture of the starting materials, the resulting solution is filtered and pH is adjusted to approximately 8.5 and then to 7.8, after which the neutralized solution is filtered again. The pH is further adjusted to approximately 7.5 after the solution is diluted. Such process yields a mixture of peptides and nucleic acids having molecular weights in a range of approximately 1to 25 KDa.

As taught by U.S. Pat. No. 5,849,196, the components over 15 KDa of the conventional composition of RETICULOSE® are more effective in treating viral diseases such as HIV, influenza virus, herpes simplex virus, etc. while the components in a range of approximately 1 to 15 KDa function as phagocytosis inhibitors.

However, the conventional methods suffers from several disadvantages: 1) the method does not ensure that each preparation produces the finished components having the same ratio, thereby the product is not reproducible; 2) the conventional method produces a wide range of the finished components, which makes the quality control of the preparation extremely difficult, if possible, because too many parameters need to be determined; 3) the presence of the higher molecular weight components, such as 25 KDa component, essentially peptides, increases the risk of hypersensitivity or immune reaction and renders the product less stable.

Therefore, it is desirable to have a product devoid of the deficiencies of conventional RETICULOSE® while maintaining its therapeutic properties. It is also desirable to identify and isolate active ingredients or components from such product so that the mode of action of Product R can be further studied and new therapeutic agents can be developed.

SUMMARY OF THE INVENTION

Accordingly, an object of the present invention is directed to novel compounds identified and isolated from the composition Product R that is described in U.S. patent application Ser. No. 09/344,095. The novel compounds have a structure comprising a polypeptide covalently bound to an oligo-nucleotide.

Another object of the present invention is directed to a novel peptide that exhibits therapeutic effect.

A further object of the present invention is directed to the therapeutic uses of these novel nucleotide-peptide and/or peptide compounds for treating diseases such as viral infections or immune system disorders.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Preparation of Product R

Figure 1:
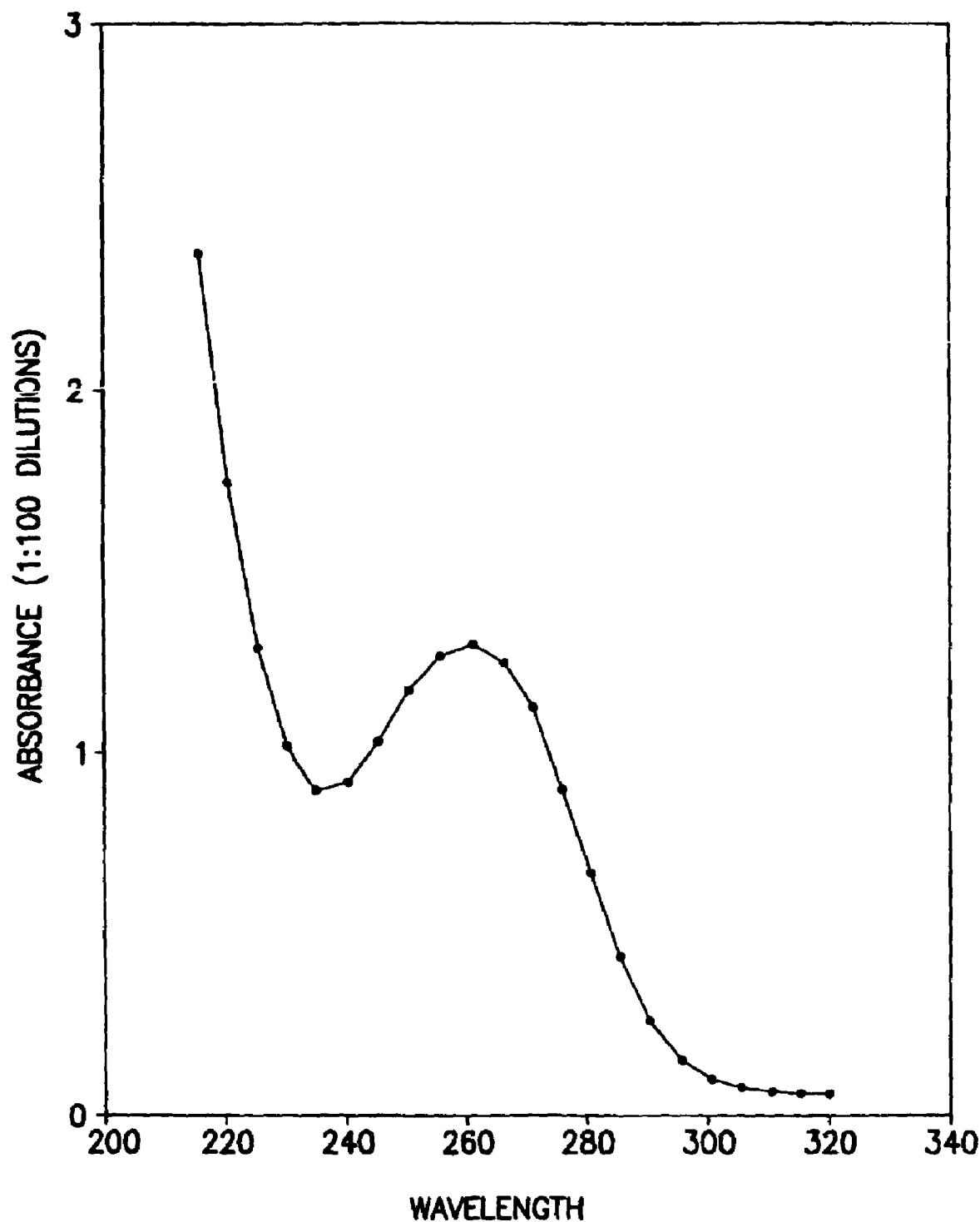
FIG. 1 shows a representative ultraviolet absorption profile of Product R.

Generally, Product R is prepared according to the following manner.

First, the starting materials casein, beef peptone, RNA, BSA, and sodium hydroxide are suspended in proportions of, by weight, 35-50% (casein), 15-40% (beef peptone), 10-25% (RNA), 1-10% (BSA) and 5-25% (sodium hydroxide) in an appropriate volume of distilled water. All starting materials are generally available or otherwise can be readily prepared by a person of ordinary skill in the art. While any RNA is suitable for the intended purpose of the present invention, plant RNA is preferred and yeast RNA is the most preferred. The ratio of total proteins versus the volume of distilled water is generally about 1.5-2.5 to about 100 by weight, preferably about 2.2 to about 100 by weight. This means that every 1.5-2.5 grams of the total proteins are suspended in about 100 milliliters of distilled water.

All the starting materials are either generally commercially available or can be readily prepared by a person of ordinary skill in the art.

The suspension as prepared above is then autoclaved at a pressure of approximately 5-15 lbs., preferably 8-10 lbs. under an elevated temperature in a range, for example about 150-300° F., preferably about 200-230° F., over a period of approximately 2-10 hours, preferably more than 3 hours. As known to a person of ordinary skill in the art, under such conditions RNA may be completely hydrolyzed into nucleotides. After autoclaving, the solution is cooled down to room temperature, and then allowed to stay at a temperature of 3 to 8° C. for at least 12 hours to precipitate insoluble elements. Alternatively, the cooled solution may be centrifuged at a temperature below 8° C. to remove the precipitates.

The resulting solution is then filtered through a 2 micron and a 0.45 micron filters under an inert gas such as nitrogen or argon at a pressure of about 1-6 psi. In a similar manner the solution is filtered again through a pyrogen retention filter, preferably 0.2 micron.

After the above filtration, the solution may be cooled at 3 to 8° C. again for at least about 12 hours and filtered again in the same way as described above.

The resulting filtrate is then assayed for total nitrogen content using methods known to a person of ordinary skill in the art such as Kjeldahl method, J.G.C.D. Kjeldahl, Z. Anal. Chem., Vol. 22, p366 (1883), and its improvements. Based on the assay, the filtrate is then diluted with chilled distilled water to an appropriate volume having a preferred total nitrogen content ranging from 165 to 210 mg/ml.

The pH of the diluted solution is then adjusted with HCl to a physiologically acceptable pH, preferably to about 7.3 to 7.6, after which the diluted solution is filtered again through a 0.2 micron filter under an inert gas as described above.

Product R so produced contains essentially nucleotides, nucleosides and free nucleic acid bases of low molecular weights from a complete hydrolysis of RNA and small peptides from partial hydrolysis of the proteins. It is possible that the base hydrolysis of the proteins also produces free amino acids.

It is understood that the use of filtration technique is essentially to remove bacteria or other particles having similar size to or larger size than bacteria. Thus, any filter regardless its manufacturer or material from which it is made is suitable for the intended purpose. All filters used in the present process are widely available to a person of ordinary skill in the art.

The final filtrate is then filled and sealed into appropriate vials, such as 2 ml or 10ml glass vials under an inert gas. The filled vials are autoclaved for final sterilization, after which they are ready for use.

In use, Product R is administered parenterally or topically to a patient in need as described, for example, in U.S. Pat. Nos. 5,807,839, 5,807,840 and 5,902,786, the contents of which are herein incorporated by reference in their entirety. However, the uses of Product R are not limited to those disclosed in the above patents.

An analysis of the composition of Product R reveals that Product R contains two major components, which are exhibited as two bands having molecular weights of 5.2 KDa and 4.3 KDa on a SDS-polyacrymide gel electrophoresis, namely peptide-A and peptide-B, respectively. Peptide-A is a novel single peptide and peptide-B comprises a single peptide covalently bound to an oligo-nucleotide. These two components are in a relatively equal amount by weight.

Functional analysis of these two components demonstrated that both of them are capable of inducing the production of interlukin-8 (IL-8) and monocyte chemotactic protein 1(MCP-1) in U937 cells, while peptide-B contributes more to the activity than peptide-A. The combined activity of these two components is comparable with Product R, indicating that these two peptide-nucleotide components are likely to be the key ingredients responsible for all biological activities of Product R.

Characterization of Product R

The ultraviolet absorption spectrum: FIG. 1 is a representative ultraviolet absorption spectrum of Product R measured in 1 cm path length quartz microcuvette (100 µl capacity) using a Shimadzu Model UV-1201 UV-VIS Spectrophotometer. Product R was diluted with distilled water by 100 fold. The spectrum is recorded between 220-320 nm and shows a maximum absorption at 260 nm and a trough at 235 nm. The ratio of the absorbance (A) at 260 nm over absorbance at 280 nm is 1.998 (±10%), and A at 260 nm over A at 230nm is 1.359 (±10%).

Figure 2:
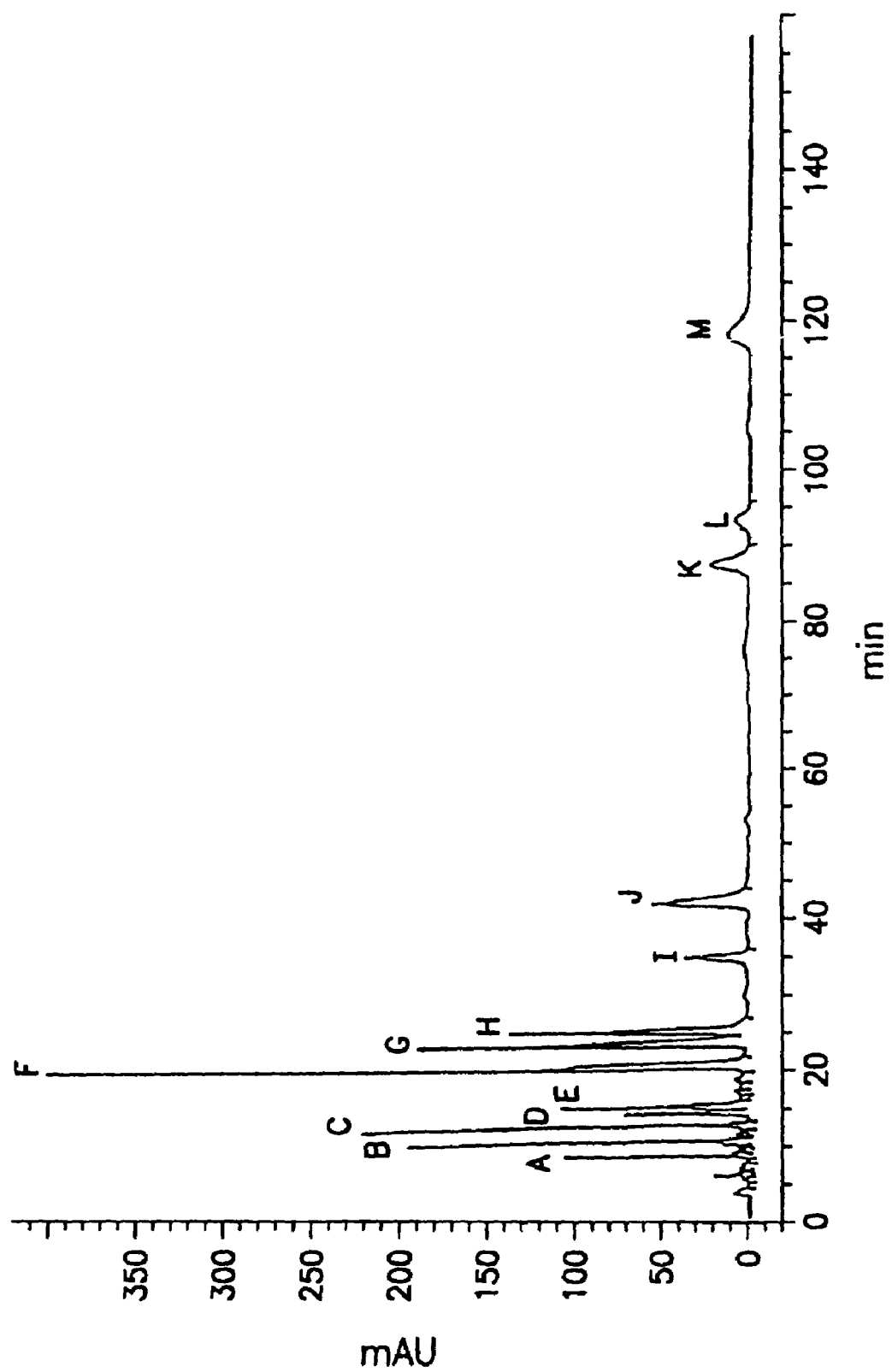
FIG. 2 shows a representative chromatogram of Product R obtained form a reverse phase HPLC analysis.

The HPLC profile: FIG. 2 is a representative chromatogram of Product R obtained from a reverse phase HPLC analysis using a Hewlett Packard 1100 HPLC system (Hewlett Packard Co.) that includes a binary pump (Model G1312A), a diode array detector (Model G1315A), a column thermostat (Model G 1316A), a thermostatted autosampler (Model G1329A), a sample thermostat and a vacuum degasser (Model G 1322A); and a stainless steel YMC-pack ODS-AQ S-5 uM column (YMC, Inc. 3223 Burnt Mill Dr., Wilmington, N.C. 28403) that has a size of 250×10 mm ID and pore size 120 A. The mobile phase consisting of a 0.1 M acetic acid: trietheylamine is prepared as follows: 6.0 ml of glacial acetic acid are dissolved in 1000 ml of HPLC grade water. The stirred solution of acetic acid is titrated with triethylamine to pH 4.8. The solution is allowed to equilibrate overnight at room temperature and then filtered through a 0.45 µM pore size and 52 mm diameter filter. The pH of the solution is readjusted to pH 4.8 if necessary with the addition of triethylamine prior to use. The mobile phase is degassed by the vacuum degasser built into the HPLC flow system. 8 µl of Product R sample are injected, by means of an autosampler, into the column having a temperature set at 30° C. for each injection. The sample is then isocratically eluted from the column with 0.1 M acetic acid: triethylamine mobile phase (pH 4.8) at a rate of 1 ml per minute under a pump pressure of 92-102 bar. The chromatograms (UV absorbences at 260 nm) are run at 160 minutes per sample and the data are collected by the diode array detector and then analyzed using Hewlett-Packard HPLC ChemStation software. Graphical plots are generated and statistical analysis is conducted using the SigmaPlot program. The reverse phase HPLC under such conditions results in 13 characteristic HPLC peaks: A, B, C, D, E, F, G, H, I, J, K, L and M, each of which has a characteristic UV absorption profile (data not shown).

Figure 3:
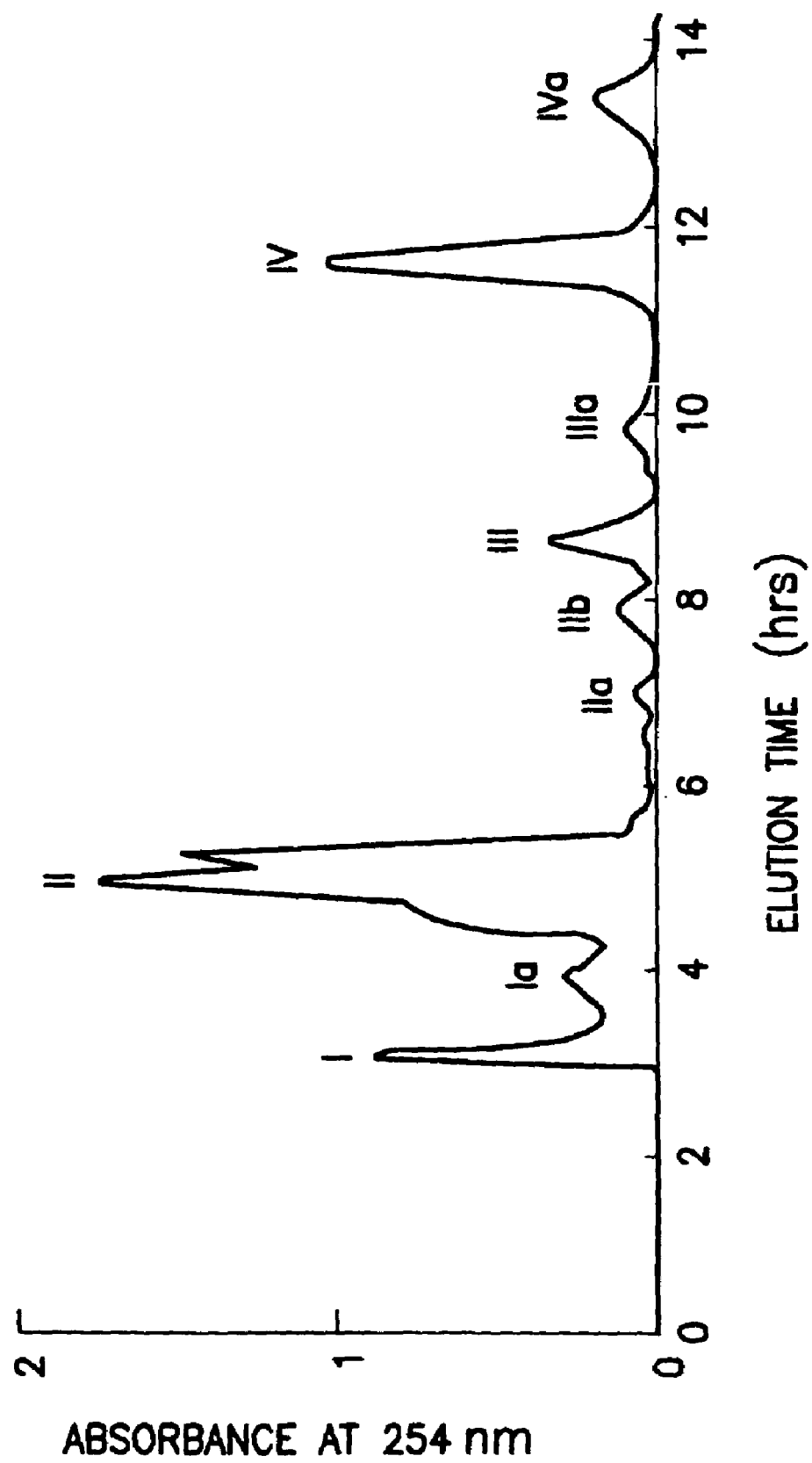
FIG. 3 shows a BioGel P-2 fractionation profile of Product R.

The BioGel P-2 gel filtration profile: FIG. 3 shows a fractionation profile of Product R on a BioGel P-2 (Bio-Rad Laboratories Inc.) column having a size of 2.6 cm×55 cm packed size. After loading of Product R to the column, the column is eluted with a 0.1× PBS, preferably DULBECCO's PBS, free of calcium ion ($Ca^{++}$) and magnesium ion ($Mg^{++}$), at a flow rate of 0.5 milliliters per minute. 1× PBS contains 1.47 mM $KH_2PO_4$, 2.67 mM KCl, 138 mM NaCl and 8.1 mM $Na_2HPO_4$ $7H_2O$. The eluent passes through a "Uvcord SII" monitor, which is attached to a REC 101 chart recorder and fitted with a 254 nm filter, and is collected at 12 minutes per fraction in a "Frac 200" fraction collector. The gel filtration chromatography under such conditions results in 9 fractions: I, Ia, II, IIa, IIb, III, IIIa, IV and IVa. Each individual peak is compared with known nucleotides, nucleosides and free nucleic acid bases eluted at the same or very close to the volumes of respective fractions as shown in TABLE I. Known compounds having comparable values are shown in Remarks column.

TABLE I

| Peak | λmax | λmin | $A_{260}/A_{280}$ | $A_{260}/A_{230}$ | Remarks |
|---|---|---|---|---|---|
| Peak I | ~275 nm | ~255 nm | 0.976 | 0.300 | Mostly peptides and peptide conjugates |
| Peak Ia | ~260 nm | ~240 nm | 1.636 | 0.943 | Nucleoprotein and/peptide nucleic acid |
| Peak Is | ~270 nm | ~245 nm | 1.258 | 0.939 | Major component is CMP |
| Peak IIα | ~260 nm | ~230 nm | 2.893 | 3.12 | Major components are AMP, UMP |
| Peak IIβ | ~250 nm | ~225 nm | 1.509 | 1.988 | Major component is GMP |
| Peak IIa | ~250 nm | ~230 nm | 1.257 | 1.176 | Mixed components |
| Peak IIb | ~270 nm | ~250 nm | 1.142 | 0.941 | Major component is Cytidine |
| Peak III | ~260 nm | ~230 nm | 2.695 | 3.664 | Major component is Uridine |
| Peak IIIa | ~260 nm | ~225 nm | 5.15 | 4.24 | Major components are Uracil, Adenosine |
| Peak IV | ~260 nm | ~225 nm | 5.406 | 3.892 | Major component is Adenine |
| Peak IVa | ~245 nm | ~225 nm | 1.016 | 1.285 | Major component is Guanine |

Figure 4:
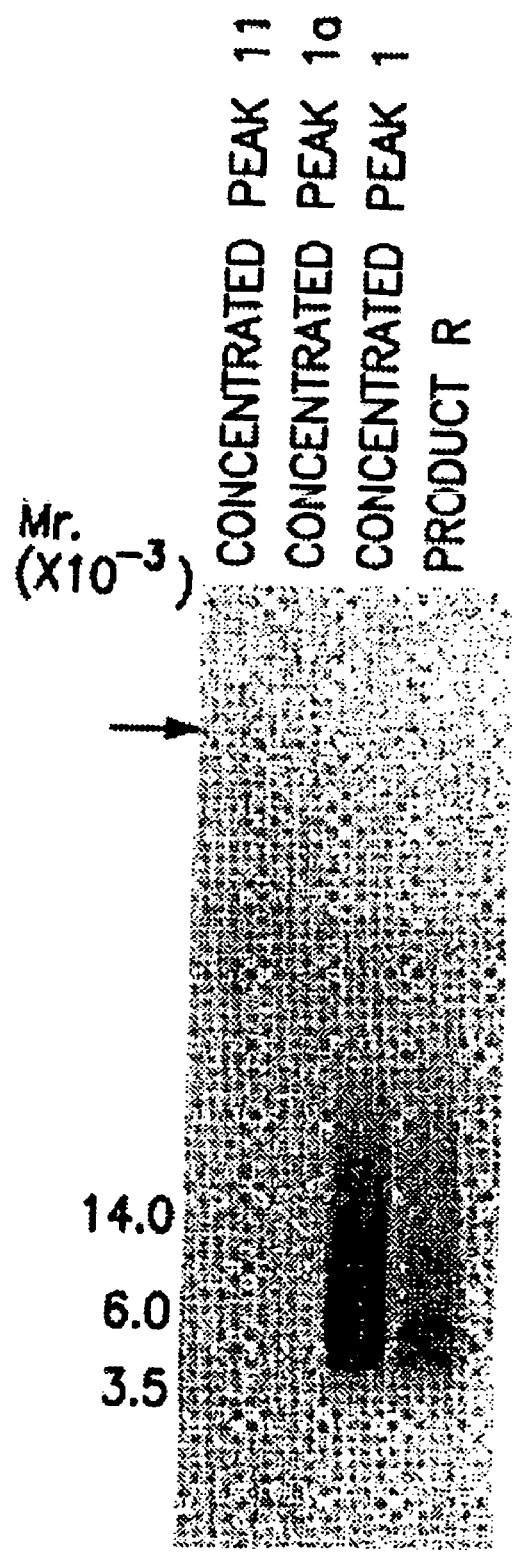
FIG. 4 shows the components of fraction I of the BioGel P-2 fractionation profile resolved on a 16% of SDS-Polyacrylamide gel electrophoresis (SDS-PAGE)

The fractions are then concentrated and analyzed by SDS-PAGE (see the following) on a 16% gel. Silver staining of the gel demonstrates that only fraction I shows essentially two major silverstainable bands having apparent molecular weights of 4.3 KDa, 5.2 KDa and a minor 7.6 KDa band as shown in FIG. 4.

Figure 5:
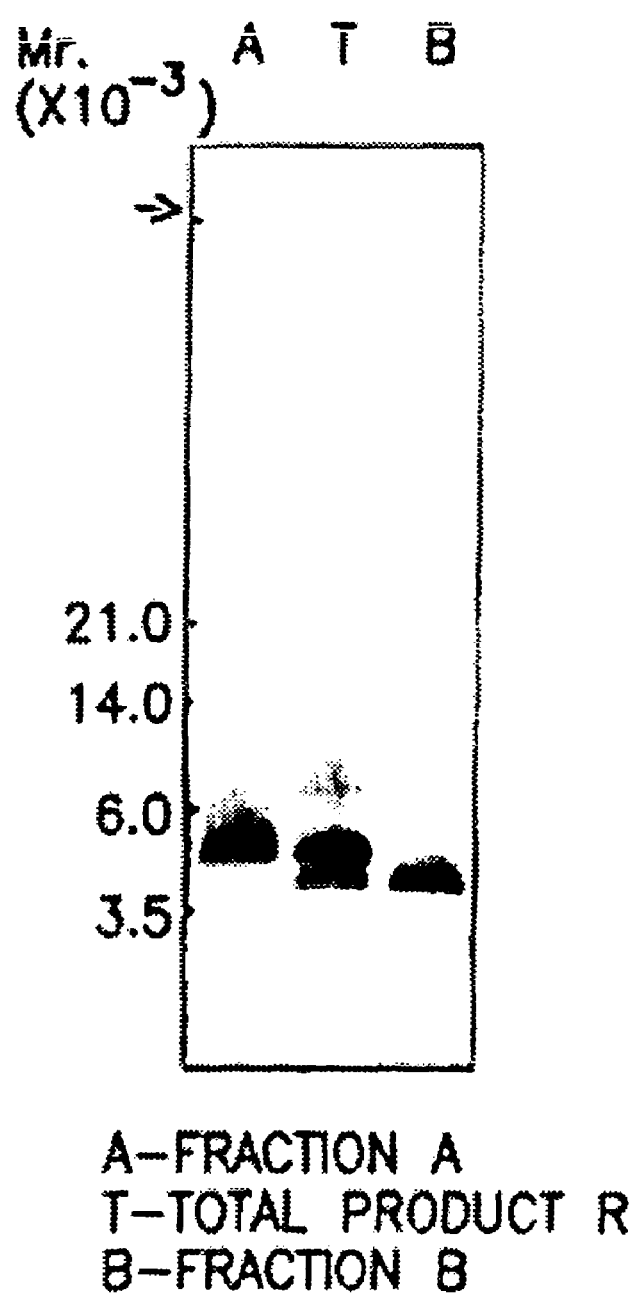
FIG. 5 shows the relative mass (Mr.) of the two major peptide components of Product R resolved on a 16% SDS-PAGE.

The relative mass (Mr.): FIG. 5 shows the relative mass (measurement of molecular weight) of the two major peptide components of Product R resolved on a 16% SDS-Polyacrylamide gel electrophoresis (SDS-PAGE) and stained by silver stain using 'SilverXpress' staining kit from NOVEX, following manufacturer-suggested protocol. Product R is resolved into two major silverstainable bands having apparent molecular weight of about 4.3 and about 5.2 KDa. A minor silver stainable component having molecular weight of about 7.6 KDa is also visible on an overloaded SDS-PAGE gel, and there may be trace amounts of other silverstainable peptides having molecular weights ranging from about 5 KDa to about 14 KDa. Coomassie Blue, a universal protein stain, stains the 4.3 KDa band extremely poorly. The three bands, 4.3 KDa, 5.2 KDa and 7.6 KDa, constitute more than about 90% of the peptides. Thus, Product R consists essentially of molecules having molecular weights below 8 KDa.

TABLE II shows the amino acid compositions of the 5.2 KDa and the 4.3 KDa components. Amino acid analysis of the 5.2 KDa band (sample A) and the 4.3 KDa band (sample B) was performed on a PE Bio-system 420 analyzer with automatic hydrolysis using standard phenyl isothiocyanite (PTIC) chemistry.

TABLE II

| Amino-Acid | Sample A Res/mol | Sample B Res/mol |
|---|---|---|
| As(x) | 1.01 | 2.03 |
| Gl(x) | 4.98 | 1.97 |
| Ser | 0.00 | 2.02 |
| His | 0.00 | 0.00 |

TABLE II-continued

| Amino-Acid | Sample A Res/mol | Sample B Res/mol |
|---|---|---|
| Gly | 0.99 | 3.99 |
| Thr | 0.00 | 0.00 |
| Ala | 2.01 | 0.99 |
| Arg | 1.03 | 1.03 |
| Tyr | 2.04 | 2.05 |
| Val | 4.01 | 3.02 |
| Met | 1.02 | 0.00 |
| Trp | 0.00 | 0.00 |
| Phe | 1.05 | 1.02 |
| Ile | 1.03 | 1.98 |
| Leu | 3.98 | 0.00 |
| Lys | 2.01 | 0.00 |
| Pro | 5.97 | 0.97 |

The biochemical properties of the peptides: Some biochemical properties of the silverstainable peptide components of Product R are analyzed using various catabolic enzymes, as described below:

The treatment with proteinase K (ICN Biochemicals): Proteinase K is a non-specific broad spectrum protease that cleaves peptide bonds at the C-terminal of aliphatic, aromatic and hydrophobic amino acids. It may cleave all serum peptides completely at 50 µg/ml within one hour. A Product R sample is incubated in a reaction buffer having 10 mM Tris-HCl, pH 7.6; 0.5% of SDS; 1 mM $CaCl_2$; 100 µg/ml of proteinase K at 40° C. for 30 minutes and then subject to SDS-PAGE on a 16% gel as described above. Under such condition, the silver stain of Product R does not show significant change. However, when the amount of proteinase K is increased to 800 µg/ml and the incubation time is extended to one hour, the 5.2 KDa band disappears but there is no obvious change of the 4.3 KDa band.

The treatment with trypsin (Boehringer Mannheim, USA): Trypsin is a serine protease, which specifically cleaves peptide bonds of lysine and arginine at the C-terminal at pH 7.5-9.0. A Product R sample is incubated in a reaction buffer having 100 mM Tris-HCl, pH 8.0, 0.1% SDS and 250 µg/ml of sequencing grade trypsin at 25° C. for 19 hours and then subject to SDS-PAGE on a 16% gel. While serum proteins will be broken down to peptides smaller than 4.3 KDa under such reaction conditions, none of the silver stained components of Product R are affected by trypsin.

The treatment with chymotrypsin (Boehringer Mannheim, USA): Chymotrypsin is a serine protease that specifically hydrolyses the peptide bonds of tyrosine, phenylalanine and tryptophan at C-terminals. It also cleaves peptide bonds of leucine, methionine, alanine, aspartic acid and glutamic acid at C-terminals at relatively lower rates. A Product R sample is incubated in a reaction buffer containing 100 mM Tris-HCl, pH 7.6, 10 mM $CaCl_2$ and 250 µg/ml of sequencing grade chymotrypsin at 25° C. for 19 hours and then subject to SDS-PAGE on a 16% gel. Chymotrypsin treatment significantly reduces the intensity of the 5.2 KDa and the 7.6 KDa bands but have no apparent effect on the 4.3 KDa band.

The treatment with pronase (Boehringer Mannheim, USA): Pronase is a non-specific protease, acts on both native and denatured proteins. It breaks down virtually all proteins into their individual amino acids. The preparation contains various types of endo-peptidases such as srine and metalloproteases, exo-peptidases such as carboypepsidases, neutral protease and neutral and alkaline phosphatases. A Product R sample is incubated in a reaction buffer containing 100 mM Tris-HCl, pH 7.4; 10 mM $CaCl_2$; 0.1% SDS and 2 mg/ml of pronase from *S. griseus* at 40° C. for 75 minutes and then subject to SDS-PAGE on a 16% gel. All silver stained components disappear after such treatment of pronase.

The treatment with N-glycosidase F (Boehringer Mannheim, USA): N-glycosidase F cleaves all types of asparagine bound N-glycans provided that the amino group and the carboxyl group are present in a peptide linkage and the oligosaccharide has the minimum length of the chitobiose core unit. A Product R sample is incubated in a reaction buffer containing 0.4× Dulbecco's PBS (where 1× PBS contains 1.47 mM KH2 $PO_4$, 2.67 mM KCl, 138 mM NaCl and 8.1 mM $Na_2$ $PO_4$ $7H_2O$), 0.1% SDS, 0.5% NP40 and 50 units/ml of recombinant N-glycosidase F at 37° C. for 4 hours and subject to SDS-PAGE on a 16% gel. The treatment N-glycosidase F does not alter the intensity of any of Product R bands on the 16% SDS gel. The resistance to N-glycosidase F indicates the lack of asparagine bound N-glycan, which is commonly observed in glycoproteins.

The treatment with ribonuclease A (ICN Biochemicals, USA): Ribonuclease A is a pyrimidine specific endoribonuclease that acts on single stranded RNA. A Product R sample is incubated in a reaction buffer containing 10 mM Tris-HCl, pH 7.4, 3 mM $MgCl_2$, and 1 mg/ml of bovine pancreatic Ribonuclease A at 37° C. for about 1 hour and subject to SDS-PAGE on a 16% gel. Ribonuclease A does not alter the intensity of any of the Product R bands resolved by 16% SDS-PAGE gel. The resistance to ribonuclease A excludes the possibility of the presence of a RNA fragment attached to the peptide.

The treatment with alkaline phosphatase (Life Technologies, USA): Calf thymus alkaline phosphatase (CIAP) is a phosphomonoesterase that hydrolyses 5'-phosphate groups from DNA, RNA and nucleotides. A Product R sample is incubated in a reaction buffer provided by the manufacturer of the enzyme and 200 units/ml CLAP at 37° C. for about one hour and subjected to SDS-PAGE on a 16% gel. CLAP does not alter the intensity of any of the Product R bands resolved by SDS-PAGE.

A summary of the above described treatments by catabolic enzymes is provided in the following TABLE III, and the results of the treatment are shown in FIG. 5, wherein "−" represents no substantial alteration of the stainable bands and "+" represents substantial alteration of the stainable bands.

TABLE III

| | Sensitivity of the Peptide Components of Product R (SDS-PAGE) | | |
|---|---|---|---|
| Enzyme | 4.3 KDa | 5.2 KDa | 7.6 KDa |
| Proteinase K (100 µg/ml) | − | +/− | ?* |
| (800 µg/ml) | − | + | ?* |
| Trypsin (250 µg/ml) | − | − | − |
| Chymotrypsin (250 µg/ml) | − | + | + |
| Pronase (2 mg/ml) | + | + | + |
| N-glycosidase F (50 units/ml) | − | − | − |
| Ribonuclease A (1 mg/ml) | − | − | − |
| Alkaline Phosphatase (200 units/ml) | − | − | − |

*This band is not clearly identified because of the presence of the enzyme fragments in that region.

The complexity of these enzymatic digestion patterns suggest that the peptide components of Product R may be conjugated with other molecules such as mono-nucleotides and/or carbohydrates, or intra/inter molecularly crosslinked.

RNA gel electrophoresis: Neither agarose nor polyacrylamide gel electrophoresis for nucleic acids generates any ethidium bromide stainable bands, indicating that there are no RNA fragments in Product R.

Figure 6:
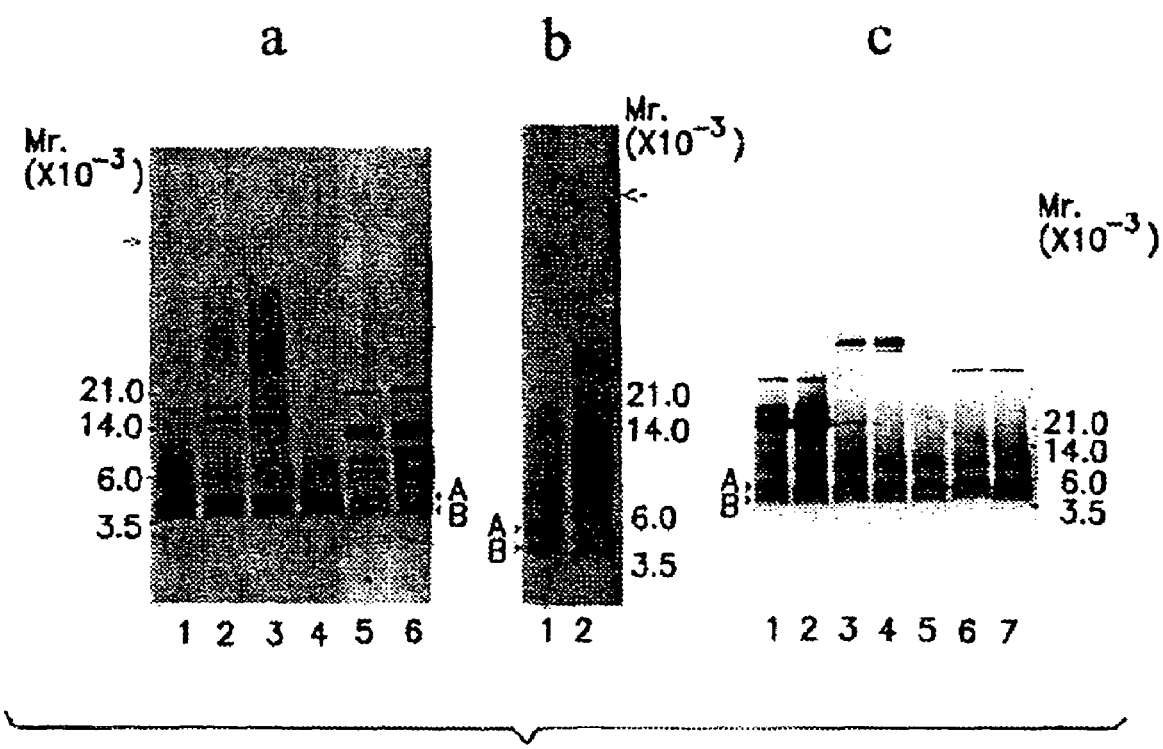
FIG. 6 is a 16% SDS-PAGE, showing the effects of a variety of catabolic enzymes on Product R.
Figure 7:
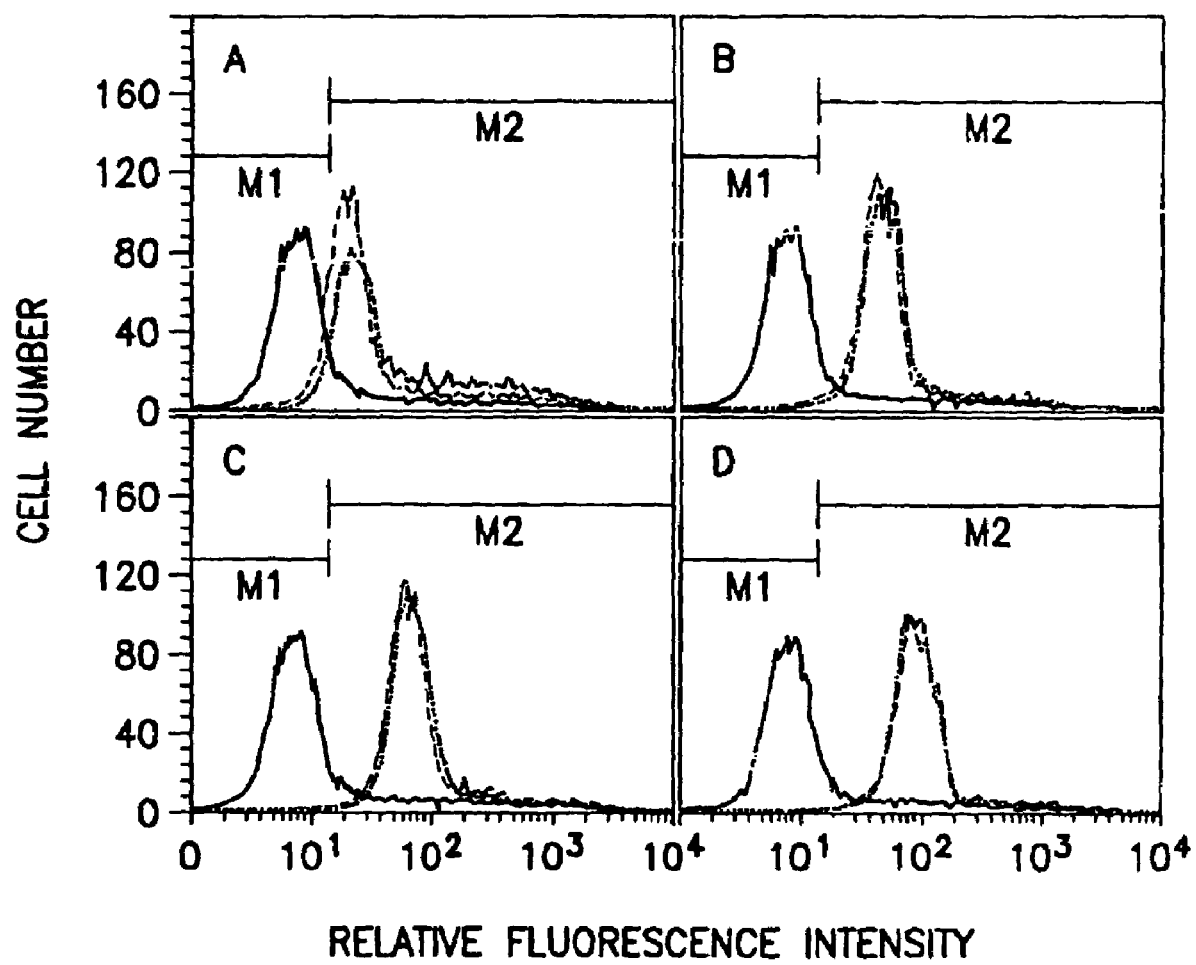
FIG. 7 is a flow cytometric histograms, showing the effect of Product R on phagocytosis of Dextran-FITC.
Figure 8:
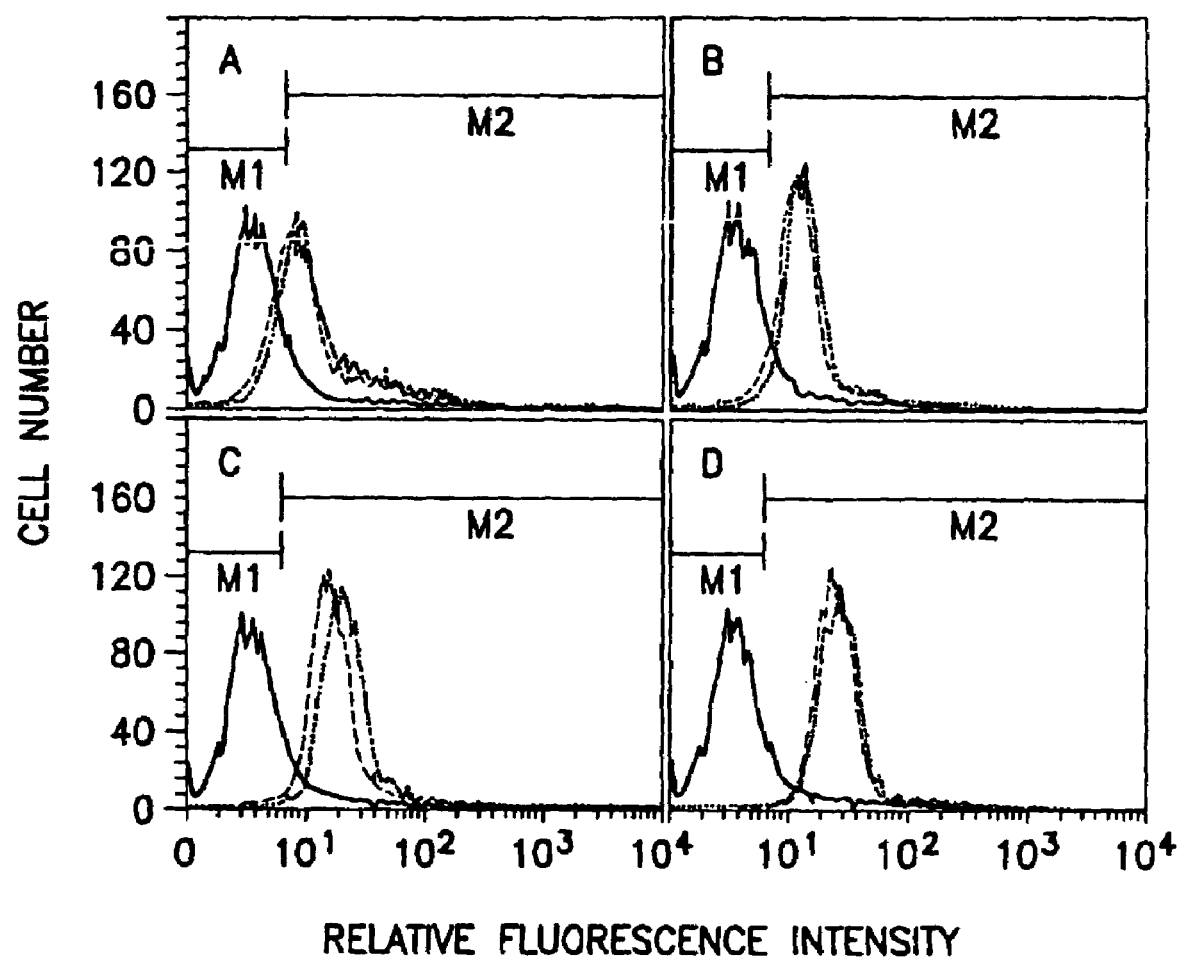
FIG. 8 is a flow cytometric histograms, showing the effect of Product R on phagocytosis of Dextran-BoDipyFL.

The effect of Product R on the phapocytosis: FIGS. 7 and 8 are flow cytometric histograms representing the cell-associated fluorescence, showing the effect of Product R on phagocytosis of Dextran-FITC or Dextran-BoDipyFL after 24 hours and 8 days of the Product R treatment, respectively. The effects of Product R on phagocytosis is tested using a human monocytic cell line, U937. The U937 cells are cultured in a medium having 5% of Product R, or 5% of PBS as a control, for 24 hours prior to the Dextran-FITC test, or 8 days prior to Dextran-BoBipyFl test. To measure phagocytosis, the cells are continuously fed with a phagocytic marker such as fluorescently-labeled Dextran-FITC for 5, 15, 30 and 45 minutes as indicated in FIG. 5, or Dextran-BoDipyFL for 5, 15, 25 and 40 minutes as indicated in FIG. 6 at 37° C. The quantity of a cell-associated fluorescence following phagocytic uptake is monitored using flow cytometry analysis according essentially to the method described by Sallusto, F. et al. (1995), J. Exp. Med., 182:389-400, which is herein incorporated by reference in its entirety. In these tests, the background values have been subtracted from those of the experimental samples and dead cells have been excluded from the data using propidium iodide exclusion.

Each of FIGS. 7 and 8 shows an overlay of the log fluorescence versus cell number for the PBS control (purple), the Product R treatment (green) and the background Dextran binding to cells (black). The purple curves (PBS control) are substantially overlapped with the green curves (Product R) at each time point, indicating that Product R does not inhibit phagocytosis of human monocytic cells.

Other biological functions of Product R: Some of other known biological functions of Product R have been described in U.S. Pat. Nos. 5,807,840, 5,807,839 and 5,902,786; U.S. patent application Ser. Nos. 08/838,077, 08/838,069, 08/835,793, 08/835,794, 08/833,950, 08/837,992, 08/837,988, 08/838,070, 08/834,190, 08/835,791, 08//838,134, 08/839,651, 08/835,796, 08/964,250, 08/964,427, 08/923,516, 08/923,343, 08/922,888, 09/189,172, 09/007,565, 09/316,624, 09/316,374, 09/257,739 and the publication by Hirschman et al., J. Investig. Med. 1996; 44:347-351. These patents, patent applications and publication are herein incorporated by references in their entireties.

Conclusions

It is thus determined that the composition of Product R prepared according to the present described methods comprises nucleotides and peptides having molecular weights not more than 14 KDa, primarily not more than 8 KDa. The peptide components of Product R are unevenly distributed and typically located at two major silverstainable bands having molecular weights of 4.3 KDa, 5.2 KDa and a minor band of 7.6 KDa.

The UV absorption spectrum of Product R typically shows a maximum absorption at 260 nm and a trough at 235 nm, and the characteristic ratios of the absorbance at 260 nm over absorbance at 280 nm is 1.998 and at 260 nm over 230 nm is 1.359.

The HPLC profile of Product R comprises fractions of A, B, C, D, E, F, G, H. I. J. K, L and M as shown in FIG. 2.

The BioGel P-2 Gel filtration profile of Product R comprises fractions of I, Ia, II, IIa, IIb, III, IIIa, IV and IVa as shown in FIG. 3.

Comparison Between the Conventional Composition of RETICULOSE® and Product R

The composition of Product R as made according to the teachings of the present invention is compared with the conventional composition of RETICULOSE® with respect to their molecular weights (MW) and ultraviolet (UV) absorbancies (A) at wavelength of 230nm, 260 nm and 280 nm, as shown in TABLE IV. While the components having molecular weights below 15 KDa of RETICULOSE® have been reported to inhibit the phagocytosis, the present application demonstrates that Product R does not inhibit the phagocytosis.

TABLE IV

|  | MW | UV | | I/PH* |
|---|---|---|---|---|
|  |  | $A_{260/280}$ | $A_{260/230}$ |  |
| Product R | <14 KDa | 1.998 | 1.359 | No |
| RETICULOSE ® | 1-25 KDa | 2.839 | 1.198 | Yes |

*inhibition of phagocytosis by molecules having molecular weight below 15 KDa

Thus, Product R differs substantially from RETICULOSE® in their composition and biological functions.

TABLE V is a comparison between the relative amounts of the starting materials used for the preparations of the present therapeutic composition Product R and the conventional composition RETICULOSE®.

TABLE V

| STARTING MATERIALS FOR INITIAL REACTION IN TEN LITERS | RETICULOSE ® | Product R |
|---|---|---|
| casein | 250 grams | 140 grams |
| beef peptone | 150 grams | 68.4 grams |
| serum albumin | 15 grams | 13 grams |
| RNA | 80 grams | 88 grams |
| NaOH | 75 grams | 66 grams |

About 221 grams proteins are used in the initial reaction for the preparation of Product R, while about 415 grams for the preparation of RETICULOSE®. Thus, the initial protein concentration for the RETICULOSE® preparation is twice as much as that for the Product R preparation.

To further study the structures and activities of Product R composition, the two major peptide components, namely the 5.2 KDa peptide (hereinafter "peptide-A") and the 4.3 KDa peptide (hereinafter "peptide-B"), were isolated and purified. A method was developed to resolve the Product R mixture and purify each of the two peptides. This involved gel filtration, followed by a lyophilization, centrifugal filtration and dialysis. This produced Peptide-A and Peptide-B samples suitable for sequencing procedures and the NMR and mass spectroscopy structural studies. Peptide-A and peptide-B are present in the Product R composition in an approximately equal amount and the total amount of these two peptides is about 4.8-5.3 mg/ml, determined by a Lowry protein assay.

Purification of Product R peptides

Product R (6 ml) was lyophilized and the lyophilization cake was dissolved in a total volume of 1.5 mL of Nanopure water to make up a 4X concentration. A BioGel P-b column (16×51 cm) was equilibrated with 0.05× Dulbecco's phosphate buffered saline, $Ca^{++}$ and $Mg^{++}$ free (PBS). Concentrated Product R was applied to the column. The column was eluted with 0.05× PBS, 1 ml fractions were collected. Fractions were tested for the presence of Peptide-A and Peptide-B by the SDS-polyacrylamide gel electrophoresis (SDS-PAGE) technique, followed by silver staining of the gel.

Fractions containing Peptide-A were pooled, and then lyophilized. Fractions containing Peptide B were not completely free of Peptide A. Fractions containing >80% of Peptide-B were pooled and lyophilized. The above process was repeated several times until sufficient amounts of individual peptides were obtained for structural studies.

Combined pools of lyophilized Peptide-A were dissolved in Nanopure water, concentrated and further purified by centrifugation through a Centriplus 3 (MWCO-3 kDa) filter assembly (Millipore Corporation, USA). The protein content of the concentrate was assayed using the BioRad DC Protein assay Kit. The purity of the Peptide-A was re-examined by SDS-PAGE, and the sample was lyophilized and the lyophilization cake was stored refrigerated at 4° C. until use for structural studies.

Combined pools of lyophilized Peptide-B were dissolved in a small volume of Nanopure water, dialyzed against 10 mM Tris-HCl, pH 7.4 in a Spectra/Por Dispo Dialyzer (MWCO-1 kDa), obtained from Spectrum Microgen, USA. The protein content and the purity of Peptide-B in the dialysate was assayed by use of the BioRad DC Protein assay kit and by SDS-PAGE, as mentioned for Peptide-A. The dialysate was lyophilized and the lyophilization cake of Peptide-B was stored refrigerated at 4° C. until use for structural studies.

Peptide-A was analyzed by NMR spectroscopy, N-terminal sequencing by the Edman method and by mass spectroscopy.

The Peptide-A sample was available as a lyophilized cake following dialysis as described in the purification of Peptides section. For NMR studies, the sample was dissolved in deuterium oxide. For mass spectral studies the material was dissolved in a PBS buffer.

NMR Analysis of Peptide-A

A 5.2 mg sample of Peptide-A (assayed by a Lowry Total protein assay) was dissolved in 0.5 mL D20 in a 5 mm NMR tube. The tube was vortex mixed for 30 sec. The spectrum was run on a Bruker 300 MHz instrument.

Figure 9A:
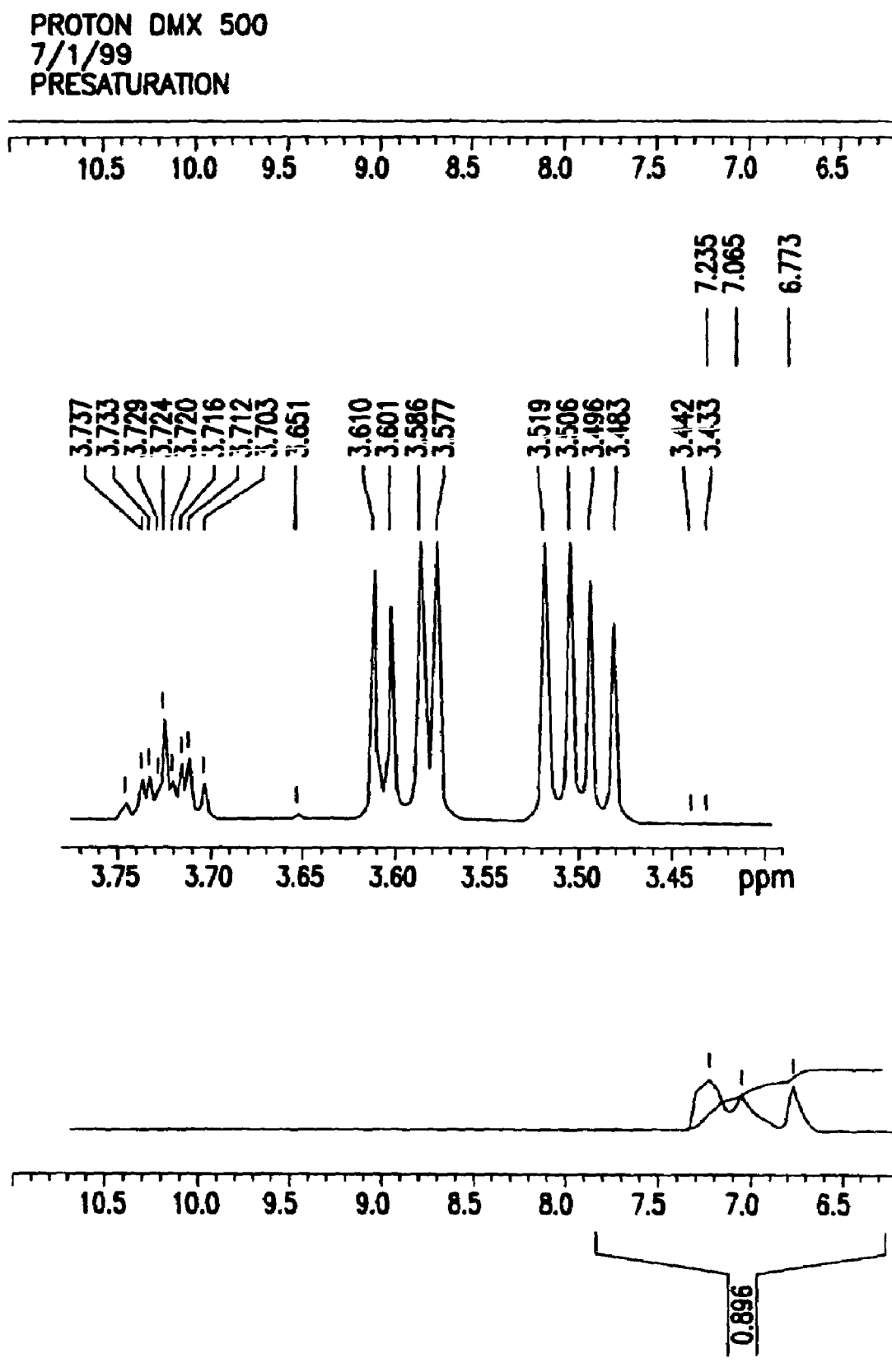
FIG. 9 is a proton NMR spectrum of Peptide-A.
Figure 9B:
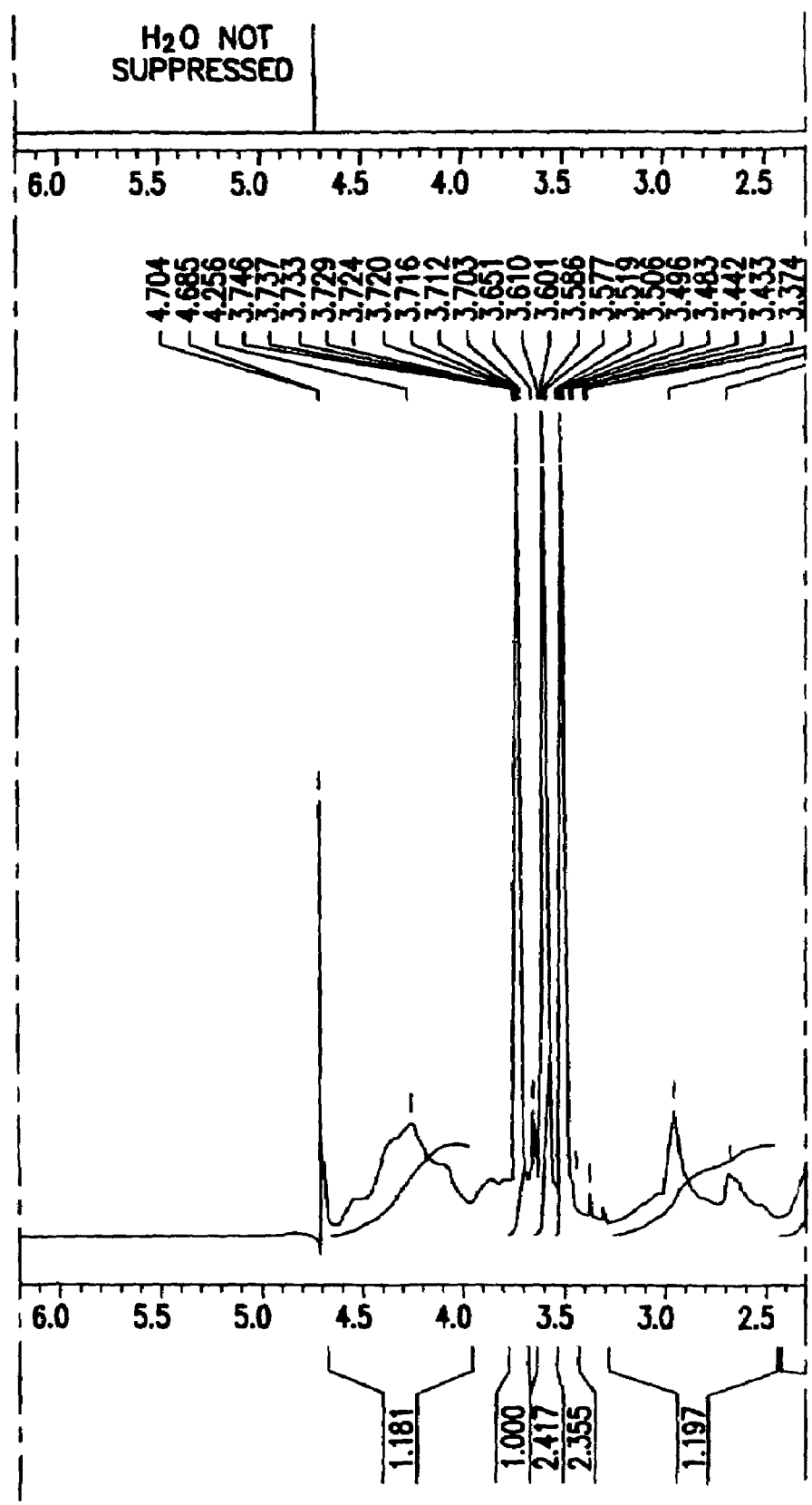
Figure 9C:
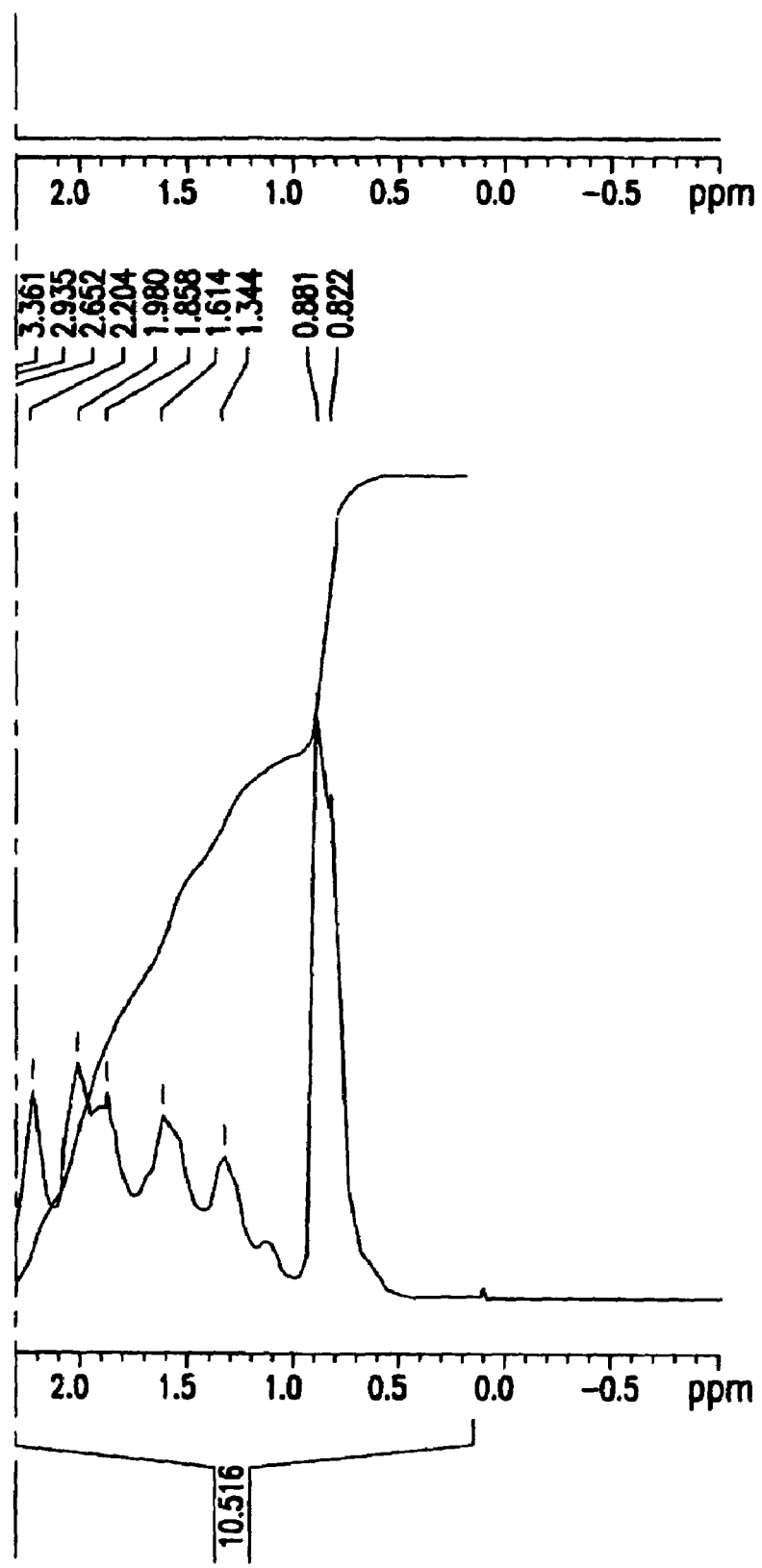

The proton NMR of Peptide-A in $D_2O$ was a typical complex spectrum of an polypeptide. Aliphatic and aromatic residues are both seen in the spectrum. (FIG. 9)

Figure 10:
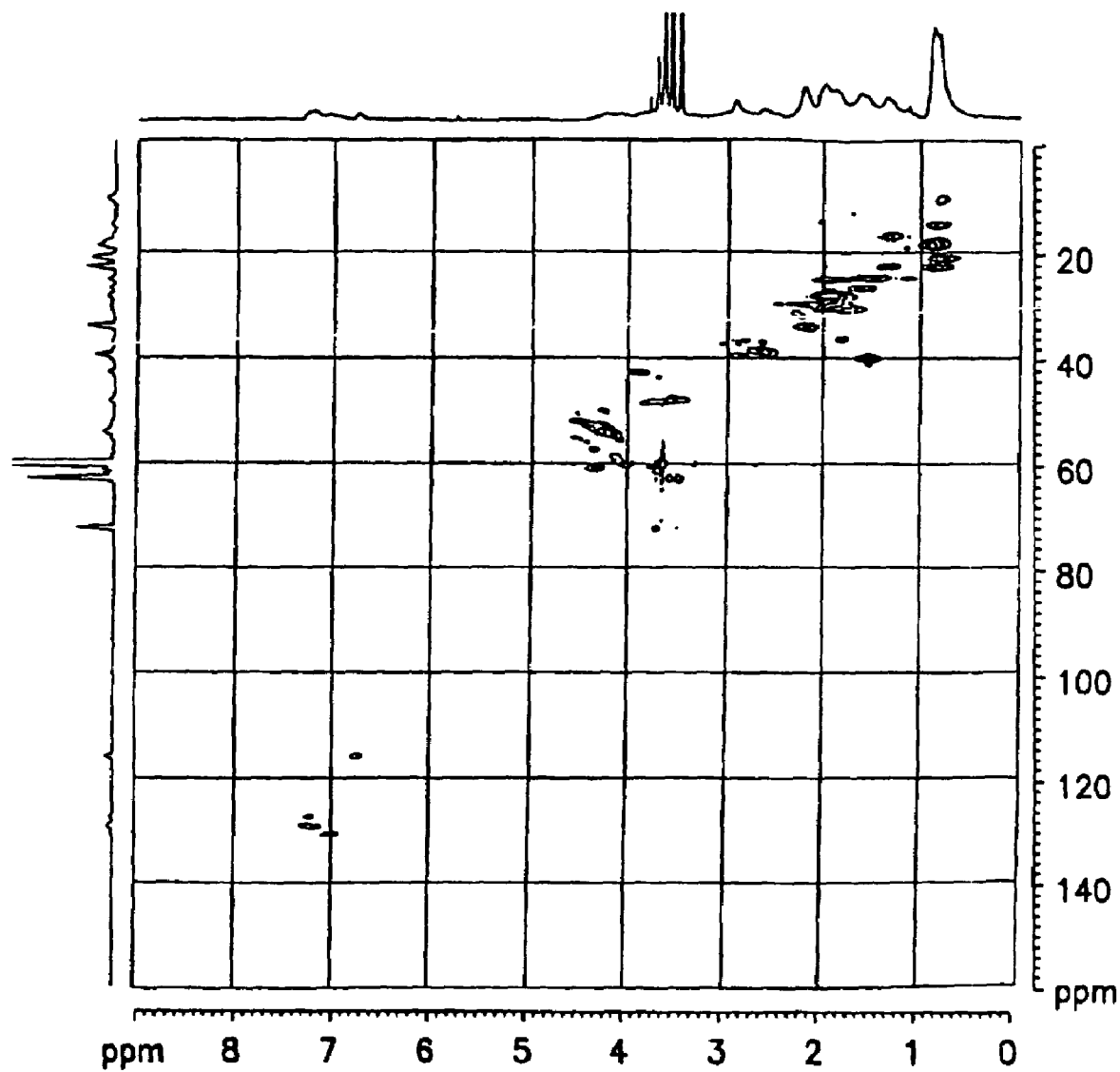
FIG. 10 is carbon/hydrogen HSQC spectrum of Peptide-A.

A $^{13}C$ carbon NMR spectrum could not satisfactorily be obtained on the sample because of low sample concentration. However, a 2D-HSQC (heteronuclear single-quantum coherence) spectrum which provides carbon atom chemical shifts for all but the tertiary carbon atoms in the sample (those lacking an attached hydrogen atom such as carbonyl groups) could be run (FIG. 10). This was carried out on a Bruker 500 MHz instrument with overnight acquisition of data over 12 hours. The two-dimensional HSQC experiment allows correlation of a proton chemical shift to the corresponding chemical shifts of the carbon atoms to which the protons are attached. This experiment resulted in elucidating the amino-acid content of Peptide A. (see TABLE VI—HSQC Spectrum Correlations—Peptide A). The HSQC 2D-spectrum indicated the presence of the aromatic amino-acids tyrosine and phenylalanine the imino-acid proline aspartic acid, glutamic acid, methionine, arginine, alanine, valine, glycine, isoleucine, leucine, lysine and glutamine as components of Peptide A. Tryptophan, cysteine, serine, asparagine, histidine or hydroxyproline could not be detected.

Assignments for the resonance chemical shifts were made on the basis of data from the following sources: K. Wuthrich, *NMR of Proteins and Nucleic Acids*, John Wiley, 1986 and J. N. S. Evans, *Biomolecular NMR Spectroscopy*, Oxford University Press, 1995).

A $^{31}P$ spectrum was also run on the Peptide-A sample; an overnight run of 12 hours produced no phosphorus resonance signals. Therefore, Peptide-A is not a phosphorylated peptide.

TABLE VI

HSQC SPECTRUM CORRELATIONS - PEPTIDE-A

CROSS PEAKS (ppm)

| PROTON | CARBON | ASSIGNMENT |
|---|---|---|
| 7.28 | 128.8 | CI Tyr |
| 7.22 | 128.4 | CI Tyr |
| 7.18 | 127.8 | C2,6 Tyr |
| 7.05 | 130.2 | C4 Phe |
| 6.75 | 115.7 | C3,5 Tyr |
| 4.60 | 55.2 | —H Asp |
| 4.52 | 54.1 | —C Met |
| 4.32 | 56.1 | —C Glu |
| 4.24 | 50.4 | —C Ma |
| 4.22 | 54.4 | —C Arg |
| 4.18 | 60.8 | —C Val |
| 3.87 | 43.0 | —C Gly |
| 3.55 | 48.3 | —C Pro |
| 2.24 | 30.3 | β-C Pro |
| 2.18 | 31.8 | β-C Met |
| 2.13 | 33.5 | β-C Gln |
| 1.74 | 36.7 | β-C Ile |
| 1.72 | 29.4 | β-C Arg |
| 1.48 | 40.0 | β-C Leu |
| 1.24 | 16.2 | —C Ile |
| 0.88 | 18.5 | —C Val |
| 0.84 | 23.2, 21.6 | —C Leu |
| 0.80 | 10.9 | —C Ile |

N-Terminal Peptide Sequencing of Peptide-A

N-terminal peptide sequencing of Peptide-A by Edman-degradative analysis was carried out a. The sequence obtained was

KVLPVPQKAVPYPQRDMPIQAFLLYQEPVLG

Or

HZN-Lys-Val-Leu-Pro-Val-Pro-Gln-Lys-Ala-Val-Pro-
Tyr-Pro-Gln-Arg-Asp-Met-Pro-Ile-Gln-Ala-Phe-Leu-
Leu-Tyr-Gln-Glu-Pro-Val-Leu-Gly-OH

An examination of the protein sequence data-base BLAST (available online through the NCBIINIH) for sequence comparison provided an exact match to this sequence, which corresponds to the amino-acid residues 178-208 in bovine beta-casein, a 216-amino-acid long peptide (A. F. Stewart, J. Bonsing, C. W. Beattie, F. Shah, I. M. Willis and A. G. Mackinlay, complete nucleotide sequences of bovine alpha-s2 and beta-casein cDNAs: Comparisons with related sequence in other species Mol.Biol.Evol. 4, 231-241 1987).

This sequence appeared to be the correct sequence for Peptide-A as Product R is derived from bovine casein. Moreover, the amino-acid composition of this sequence matches the amino-acids identified as constituents of Peptide-A in the NMR studies and in the amino-acid analysis.

The peptide structure has six spaced out proline residues and four basic glutamine residues. Since proline residues in a peptide-chain can induce bends in a peptide chain, it is likely that Peptide A has a highly folded structure, which accounts for its high chemical stability and its refractory character towards proteases and peptidases.

Mass Spectral Studies on Peptide-A

A number of mass spectra were obtained on Peptide A samples,-from Borealis Laboratories and from Commonwealth Biotechnologies. Both electrospray and MALDI-TOE (Matrix-assisted Laser Desorption Ionization-Time of Flight) methods were use to acquire the mass spectra.

MALDI-TOF mass spectroscopy has several characteristics that make it effective as a complement to sequencing techniques (K. R. Williams, S. M. Samandar, K. L. Stone, M. Saylor and J. Rush, MALDI-MS as a complement to internal protein sequencing., In: *The Protein Protocols Handbook*, J. M. Walker,ed., 1996,Humana Press, Totowa, N.J., pp 541- 555). MALDI-MS has high sensitivity and often resolves fragments representing the cleavage of consecutive peptide bonds in a peptide structure, allowing sequencing and/or confirmation of sequences detected by the Edman N-terminal sequencing protocol. MALDI-MS typically gives mass accuracies of +0.25% on the mass ions, which is satisfactory for making assignments.

The table below (TABLE VII) shows mass-fragments obtained on Peptide-A that are consistent with the 31-amino-acid peptide structure described above. The mass fragments observed also confirm the previously ambiguous amino-acid residues assigned at the positions 11,15 and 20 from the Edman N-terminal sequence analysis to be P, R and Q respectively.

TABLE VII

MALDI MASS SPECTROSCOPIC DATA FOR PEPTIDE-A

| Fragment | Mass Ion Expected | Mass Ion Observed |
| --- | --- | --- |
| /MPIQAF/ | 688.87 | 690.3 |
| /VPQKAVPY/ | 884.07 | 884.5 |
|  |  | 884.2 |
| /DMPIQAFL-NH3 | 900.09 | 900.9 |
| /AFLLYQEP-28 | 935.11 | 935.9 |
| KVLPVPQKAV/ | 962.06 | 961.90 |
| /PQKAVPYPQ-NH3 | 993.15 | 992.8 |
| /PQKAVPYPQ/ | 1010.19 | 1009.3 |
| /PIQAFLLYQ | 1075.30 | 1075.70 |
|  |  | 1075.40 |
| /LPVPQKAVPY/ | 1094.35 | 1095.70 |
| /YPQRDMPIQ-NH3 | 1113.28 | 1112.1 |
|  |  | 1113.0 |
| /PQKAVPYPQR-NH3 | 1149.34 | 1150.0 |
| /PQKAVPYPQR/ | 1166.37 | 1166.80 |
| /VPQKAVPYPQR-28 | 1237.50 | 1236.5 |
| /PQKAVPYPQRD/ | 1281.46 | 1280.9 |
| /MPIQAFLLYQE-28 | 1307.60 | 1308.20 |
|  |  | 1307.1 |
| /VPQKAVPYYPQRD/ | 1380.60 | 1381.02 |
|  |  | 1380.05 |
| /PIQAFLLYQEPV/ | 1400.67 | 1399.60 |
| /DMPIQAFLLYQE-28 | 1422.69 | 1423.1 |
| /KAVPYPQRDMPIQ-28 | 1497.81 | 1499.9 |
| /MPIQAFLLYQEPV/ | 1503.42 | 1503.85 |
|  |  | 1503.42 |
| /KAVPYPQRDMPIQ/ | 1525.82 | 1526.31 |
| /VPYPQRDMPIQAF-NH3 | 1527.79 | 1527.46 |
| /MPIQAFLLYQEPV/ | 1531.86 | 1532.05 |
| /PYPQRDMPIQAFL-NH3 | 1541.82 | 1541.84 |
| /VPYPQRDMPIQAF/ | 1544.82 | 1544.63 |
| KVLPVPQKAVPYPQ/ | 1546.90 | 1545.32 |
| /DMPIQAFLLYQEP/ | 1547.82 | 1549.47 |
| /VPYPQRDMPIQAFL/ | 1558.85 | 1560.28 |

TABLE VII-continued

MALDI MASS SPECTROSCOPIC DATA FOR PEPTIDE-A

| Fragment | Mass Ion Expected | Mass Ion Observed |
| --- | --- | --- |
| /VLPVPQKAVPYPQR/ | 1574.92 | 1575.22 |
| /QRDMPIQAFFLY-NH3 | 1588.88 | 1589.0 |
| /LPVPQKAVPYPQRD/ | 1590.87 | 1590.26 |
| /QRDMPIQAFLLYQ/ | 1605.91 | 1606.05 |
| /AVPYPQRDMPIQAF/ | 1615.90 | 1614.94 |
| /DMPIQAFLLYQEPV-NH3 | 1629.92 | 1630.35 |
| /PYPQRDMPIQAFLL-28 | 1644.00 | 1643.31 |
| /PYPQRDMPIQAFLL/ | 1672.01 | 1673.13 |
| /PYPQKAVPYPQRDMP/ | 1678.02 | 1678.15 |
| /PQRDMPIQAFLLYQ-NH3 | 1685.99 | 1686.95 |
| /QKAVPYPQRDMPIQA-28 | 1697.02 | 1698.67 |
| /PVPQKAVPYPQRDMP/ | 1706.03 | 1706.7 |
| /QKAVPYPQRDMPIQA/ | 1725.03 | 1725.6 |
| /AVPYPQRDMPIQAFL/ | 1729.06 | 1730.07 |
| /QRDMPIQAFLLYQE/ | 1735.02 | 1735.57 |
| VPYPQRDMPIQAFLL-NH3 | 1754.11 | 1755.83 |
| /DMPIQAFLLYQEPVL/ | 1760.11 | 1762.11 |
| /VPYQRDMPIQAFLL/ | 1771.14 | 1770.88 |
| /LPVPQKAVPYPQRDMP/ | 1790.17 | 1789.61 |
| /KVLPVPQKVPYPQRDM-NH3 | 1801.15 | 1799.50 |
| /KVLPVPQKAVPYPQRD/ | 1818.16 | 1772.92 |
|  |  | (—CO2, —H) |
| /YPQRDMPIQAFLLYQ/ | 1866.20 | 1864.68 |
| /QKAVPYPQRDMPIQAF/ | 1872.21 | 1874.98 |
| /VLPVPQKAVPYPQRDMP-28 | 1890.31 | 1890.61 |
| /RDMPIQAFLLYQEPVL-NH3 | 1899.27 | 1897.0 |
| /PQRDMPIQAFLLYQEP/ | 1929.26 | 1929.29 |
| /VPYPQRDMPIQAFLLY/ | 1934.32 | 1936.39 |
| /QKAVPYPQRDMPIQAFL/ | 1957.36 | 1955.81 |
| /PYPQRDMPIQAFLLYQ/ | 1963.32 | 1962.80 |
| KVLPVPQKAVPYPQRDMPI/ | 2159.64 | 2207.32 |
|  |  | (+2Na, +2H) |
| /AVPYPQRDMPIQAFLLYQE/ | 2262.69 | 2263.52 |
| /PVPQKAVPYPQRDMPIQAFLLYQ-28 | 2664.40 | 2664.36 |
| /KAVPYPQRDMPIQAFLLYQEPVL/ | 2700.23 | 2724.23 (+Na) |
| KVLPVPQKAVPYPQRDMPIQAFLLYQEPVL/ | 3462.18 | 3462.67 |
| KVLPVPQKAVPYPQRDMPIQAFLLYQEPVLG | 3536.24 | 3536.84 |
|  |  | 3583.48 (+2Na) |

The mass spectral data for Peptide-A are therefore consistent with the 31-amino-acid sequence derived from beta-casein as shown above.

Thus, peptide-A, a constituent of Product R, is a 31-amino-acid long peptide derived from bovine beta-casein with a molecular weight of 3536.24 Da. It is a straight chain peptide lacking any cysteine-cysteine cross links. The structure is remarkable for six proline residues spaced throughout the molecule and four basic glutamine residues. Since proline residues can induce bends in peptide chains, the structure is likely a highly folded peptide.

Structural Studies of Peptide-B

Peptide-B was analyzed by NMR spectroscopy, N-terminal sequencing by the Edman method, C-terminal sequencing and by mass spectroscopy.

The purified Peptide-B sample was available as a lyophilized cake following dialysis, as described in Section 4.2. For NMR studies, the sample was dissolved in deuterium oxide. For mass spectral studies, the material was dissolved either in Nanopure water or in 0.1 × PBS buffer. Peptide B also gave a positive reaction for glycopeptide/nucleopeptide by treatment with periodate and labeling with DIG-hapten (Boehringer Mannheim). The DIG-hapten-bound Peptide-B was reacted with anti-DIG-peroxidase, and then treated with TETON (4-Triethylenetrioxy-1-naphthanol) to produce a blue precipitate, indicating a sugar moiety attached to the peptide portion in a glycopeptide/nucleopeptide complex.

NMR Spectral Analysis of Peptide-B

Figure 11:
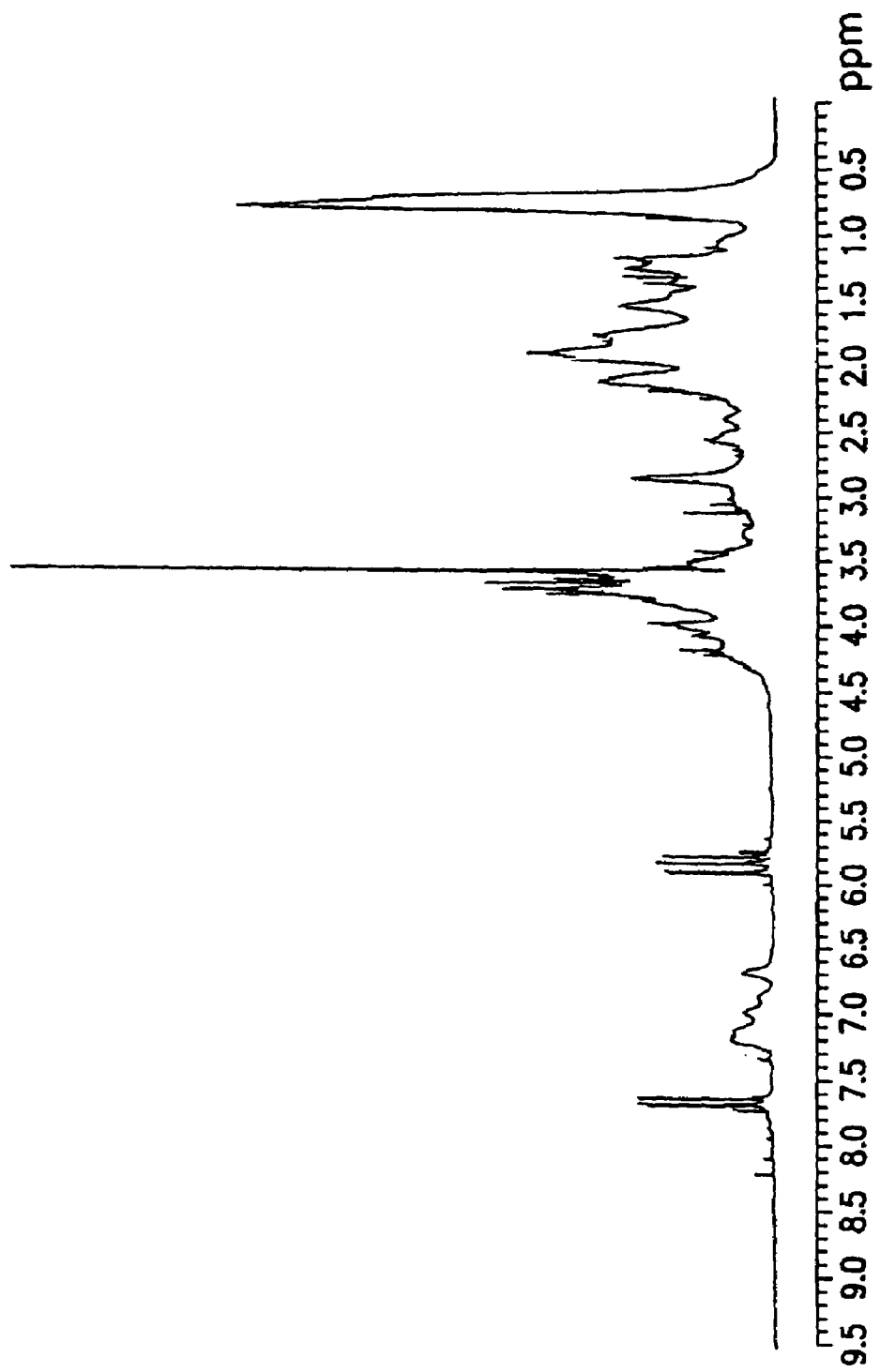
FIG. 11 is a proton NMR spectrum of Peptide-B.

The proton NMR spectrum for Peptide-B (FIG. 11) shows signals characteristic of a peptide compound, but has additional atypical peaks in the aromatic region of the spectrum not typical of any aromatic amino-acids and in the region between the 5.7-6.05 ppm region resembling those of the aromatic protons and ribose sugar residues in a diadenosine diribonucleotide. Assignments for proton resonance signals are shown in TABLE VIII. The extra non-peptide peaks in the spectrum appeared in a 1:1 molar ratio with the peptide indicating a 1:1 molar complex between a peptide and an adenosine-adenosine dinucleotide.

Figure 12:
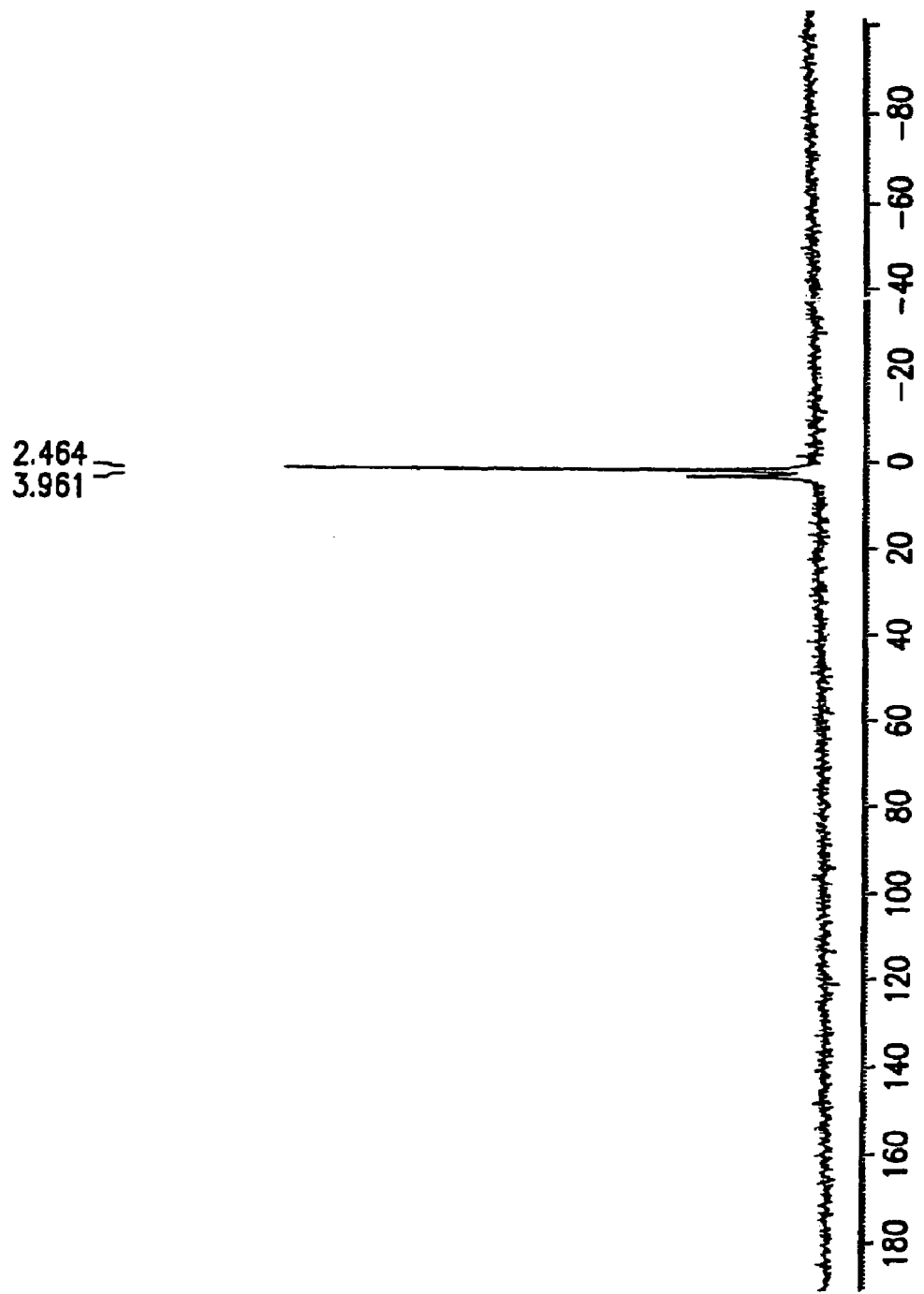
FIG. 12 is a phosphorus-31 NMR spectrum of Peptide-B.

The phosphorus spectrum (FIG. 12) shows three signals, a split peak at 3.96 ppm indicative of two phosphodiester phosphorus atoms shifted somewhat downfield from those expected of a typical internucleoside phosphodiester linkage, and another at 2.46 ppm charactersitic of a internucleotide phosphodiester linkage. This suggests one traditional 3' to 5' phosphodiester linkage between ribose units in a ribodinucleotide unit together with two other phosphodiester bonds that are not typical internucleotide linkages. It is therefore likely that a covalent phosphodiester linkage exists through a hydroxyl group on a seine or tyrosine residue to a hydroxyl group on the ribose moiety of the dinucleotide.

Figure 13:
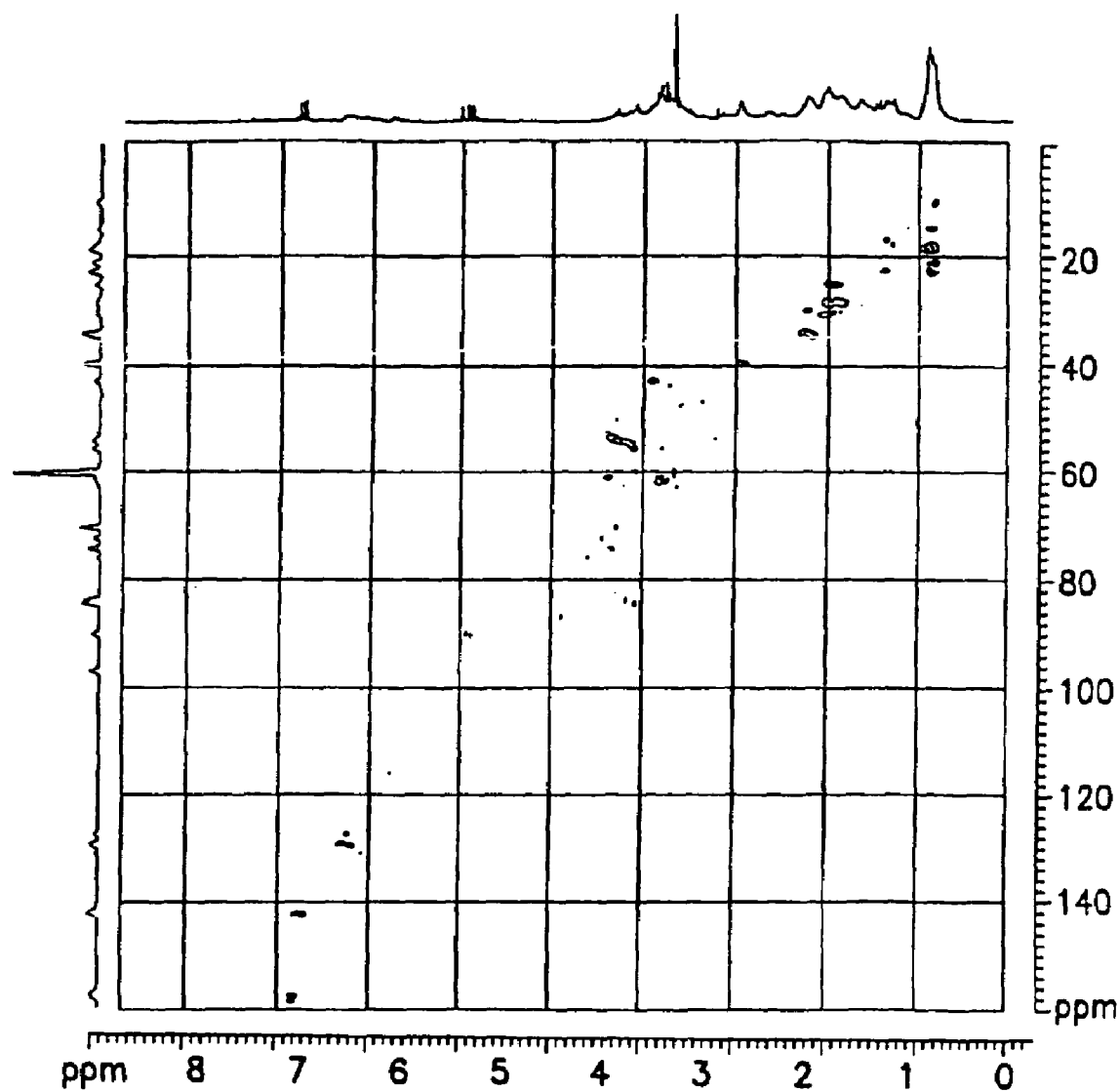
FIG. 13 is a carbon/hydrogen HSQC spectrum of Peptide-B.

Peptide-B therefore consists of a peptide unit linked to a diadenosine ribodinucleotide, as it shows NMR signals corresponding to amino-acids and adenine units. Amino-acids identified from the HSQC spectrum (FIG. 13, TABLE X) are 4 glycine residues, 3 valine residues, 3 aspartic acid residues, 2 isoleucine residues, 2 seine residues, 2tyrosine residues, and one each of alanine, arginine, phenylalanine, proline and glutamic acid. These data, taken together, indicate a 21-amino-acid long peptide associated with an adenine diribonucleotide attachment, possibly through a diphosphodiester-type linkage.

Figure 14:
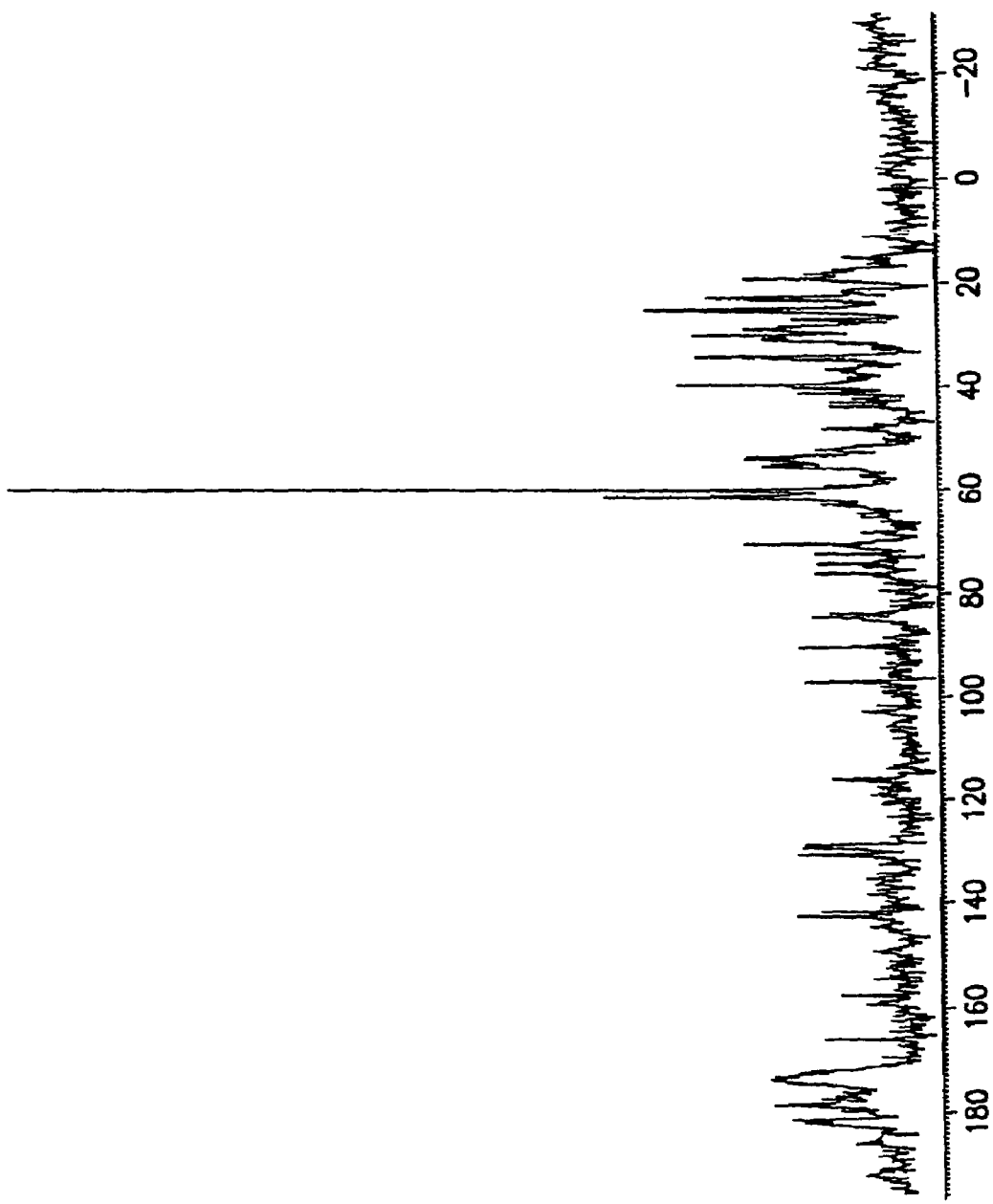
FIG. 14 is a C-13 NMR spectrum of Peptide-B.

The C-13 NMR spectrum of Peptide-B (FIG. 14, TABLE IX) similarly shows peaks atypical of any amino-acids, both in the aromatic region (118-160 ppm) corresponding to adenine and in the region of 70-90 ppm where ribose ring carbon atoms produce signals, which can be attributed to two adenosine subunits.

It was considered further that a diadenosine dinucleotide could be linked as an ionic complex to the peptide moiety and not be covalently attached. To determine if this was the case, an experiment was run to dissociate a possible dinucleotide unit attached by ionic bonding to the peptide. A sample of Peptide B was brought to a 2M-NaCl ionic strength by the addition of 5M NaCl. This high ionic-strength solution should dissociate an ionic complex. The solution was incubated at 4° C. for 1 hour and then was dialyzed against 500 mL of a 1M NaCl in 10 mM Tris-HCL, pH 7.9 solution in a Float-a-Lyzer bag (MW cut-off—IkDa) for 2 hours. The dialysate was then re-dialyzed at 40° C. for 2 hours against 500 mL of a 0.5M NaCl solution in 10 mM Tris-HCl, pH 7.9. A final dialysis at 4° C. for 16 hours overnight against 2.5 L of 10 mM Tris-HCl, pH 7.9 provided a solution of Peptide-B which was applied to a Macroprep DEAE support column previously equilibrated with 10 mM Tris-HCl. The eluate solution was lyophilized. This product was then again analyzed by proton and phosphorus NMR and gave identical spectra to that of untreated Peptide-B. This suggests a covalent rather than an ionic complex between the peptide and oligonucleotide moieties connected through a phosphodiester linkage through a hydroxyl group on an amino-acid residue.

N-Terminal Sequence Analysis of Peptide-B

N-terminal peptide sequencing of Peptide-B by Edman degradative analysis was carried out. The sample was dissolved in 1 mL of Nanopure water and of the dissolved sample, 50 µL were applied to sequencing cartridges. A 30 cycle sequence was run, which resulted in the identification of a 21-amino acid-long sequence:

GEIPDAGGR1VDYYVGFSD(X)(X)

The amino-acids at the C-terminal ends, 20 and 21 could not be unambiguously determined in the sequence. This sequence was searched in the NCBI/BLAST database but resulted in no hits for any matching sequences. Thus Peptide-B appears to be a previously undescribed compound.

TABLE VIII

Proton NMR peak assignments for Peptide B (in $H_2O$ olution)

| Chemical Shift | Peak Assignment |
|---|---|
| 0.897 | —$CH_3$ Ile (2 ile residues) |
| 0.909 | |
| 0.933 | |
| 0.947 | —$CH_3$ Val, —$CH_3$ Ile (3 Val, 2 Ile residues) |
| 0.949 | |
| 0.946 | |
| 0.964 | |
| 1.409 | β-H Ala |
| 1.476 | |
| 1.490 | —$CH_2$ Ile (2 Ile residues) |
| 1.676 | γ-$CH_2$ Arg |
| 1.866 | β-H Asp (3 Asp residues) |
| 1.885 | |
| 1.920 | |
| 2.011 | β-H Pro |
| 2.071 | β-H Glu |
| 2.164 | β-H Val (3 Val residues) |
| 2.178 | |
| 2.191 | |
| 2.284 | β-H Pro |
| 2.299 | —$CH_2$ Glu |
| 2.961 | β-H Tyr |
| 3 151 | β-H Phe |
| 3.696 | —H Pro |
| 3.706 | Ribose 5' $CH_2OH$ |
| 3.878 | β-H Ser (2 Ser residues) |
| 3.885 | |
| 3.901 | —H Gly (4 Gly residues) |
| 3.912 | |
| 3.923 | |
| 3.931 | |
| 4.158 | —H Val (3 Val residues) |
| 4.178 | |
| 4.166 | —H Glu |
| 4.323 | |
| 4.359 | —H Arg |
| 4.425 | —H Pro |
| 5.863 | Ribose 5' |
| 5.886 | Ribose 3' |
| 5.894 | |
| 5.938 | Ribose 2' |
| 5.948 | |
| 6.006 | Ribose 1' |
| 6.021 | |
| 6.794 | 3,5-H Tyr |
| 7.088 | |
| 7.144 | 2,6-H, Tyr |
| 7,266 | 2,6-H, Phe |
| 7,282 | 3,5-H, Phe |
| 7,305 | 4-H, Phe |

TABLE VIII-continued

Proton NMR peak assignments for Peptide B (in H₂0 olution)

| Chemical Shift | Peak Assignment |
|---|---|
| 7.740 | Adenine ring H-2 |
| 7.756 | |
| 7.791 | Adenine ring H8 |
| 7.806 | |

TABLE IX

C13 NMR PEAK ASSIGNMENTS FOR PEPTIDE B (IN D₂O)

| Chemical Shift (ppm) | Peak Assignment |
|---|---|
| 17.7 | Ala (—C) |
| 18.5 | Val (—C) |
| 23.2 | Pro (—C) |
| 25.7 | Arg (—C) |
| 28.7 | Arg (—C) |
| 28.8 | Glu (—C) |
| 30.6 | Pro (—C) |
| 38.4 | Tyr (—C)/Phe (—C) |
| 39.8 | Asp (—C) |
| 40.8 | Asp (—C) |
| 41.7 | Arg (—C) |
| 43.5 | Gly (—C) |
| 43.9 | Gly (—C) |
| 48.2 | Pro (trans, —C) |
| 51.2 | Ala (—C) |
| 53.1 | Asp (—C) |
| 53.4 | |
| 57.4 | Phe (—C), Tyr (—C) |
| 57.6 | |
| 60.0 | Ile (—C) |
| 60.8 | Val (—C) |
| 62.0 | Ribose 5' CH₂OH |
| 62.3 | Ser (—C) |
| 62.4 | |
| 72.0 | Adenosine (ribose C2') |
| 74.2 | Adenosine (ribose C3') |
| 83.7 | Adenosine (ribose C4') |
| 84.2 | |
| 90.4 | Adenosine (ribose C1') |
| 95.2 | |
| 116.2 | Tyr (C3, C5) |
| 128.4 | Tyr (C1), Phe (C-4) |
| 128.6 | |
| 131.2 | Tyr (C2, C6) |
| 141.8 | Adenine (Adenosine ring C8) |
| 142.4 | |
| 158.1 | Adenine (adenosine ring C4/C2) |
| 172-177 | Amino acid C = 0 groups |
| 182.8 | Glu (—C) |

TABLE X

HSQC SPECTRUM CORRELATIONS - PEPTIDE-B CROSS PEAKS
Chemical Shift (ppm)

| Proton | Carbon | Assignment |
|---|---|---|
| 7.79 | 158.1 | Adenosine C/H 2 |
| 7.80 | 159.4 | |
| 7.74 | 141.8 | Adenosine C/H 8 |
| 7.76 | 142.4 | |
| 7.30 | 128.4 | Phe C4 |
| 7.28 | 128.6 | Phe 2, 6 |
| 6.79 | 116.2 | Tyr 3, 5 |
| 6.01 | 95.2 | Adenosine 1' |
| 5.95 | 90.4 | Adensone 1' |
| 4.81 | 72.0 | Adenosine 2' |

TABLE X-continued

HSQC SPECTRUM CORRELATIONS - PEPTIDE-B CROSS PEAKS
Chemical Shift (ppm)

| Proton | Carbon | Assignment |
|---|---|---|
| 4.60 | 74.2 | Adenosine 3' |
| 4.38 | 53.3 | —C Leu |
| 4.28 | 70.1 | Adenosine 2' |
| 4.20 | 83.7 | Adenosine 4' |
| 4.16 | 84.2 | Adenosine 4' |
| 4.17 | 60.8 | —C/H Val |
| 3.91 | 43.5 | —C/H Gly |
| 3.89 | 62.3 | —C/H Ser |
| 3.70 | 62.0 | Adenosine 5'-CH₂OH |
| 2.96 | 39.4 | —C/H Tyr |
| 2.28 | 34.1 | —C/H Pro |
| 2.17 | 30.6 | —C/H Val |
| 2.07 | 28.8 | —C/H Glu |
| 1.89 | 25.7 | —C/H Arg |
| 1.41 | 17.7 | —C/H Ala |
| 0.93 | 19.3 | —C/H Val |
| 0.92 | 22.8 | —C/H Leu |
| 0.89 | 15.7 | —C/H Ile |
| 0.80 | 11.3 | —C/H Ile |

C-Terminal Sequence Analysis of Peptide-B and Structural Deduction

C-terminal peptide sequence analysis of Peptide-B was carried out at Commonwealth Biotechnologies, Inc. using carboxypeptidase Y digestion. An amount of 3.8 mg Peptide-B was used. Samples were incubated with carboxypeptidase Y (Sigma C 3888) which was added in a final molar ratio of 1:20 of enzyme to Peptide-B. Samples were incubated at room temperature and with increasing time (0 mm 30 mm, 1 hr, 2 hrs, 5 hrs and 16 hrs), 20 µL aliquots were removed and individually subjected to amino-acid analysis. An autolysis sample of the enzyme was subjected to the entire protocols as a control. The enzyme digestion was terminated by the addition of 5 µL of glacial acetic acid. Each sample was taken to dryness (speed-vac) and then dissolved in 50 µL of the amino-acid loading buffer and subjected to amino-acid analysis.

A time-dependent release of amino-acids was observed, reaching equivalence at about 7 picomoles. The residue released first and reaching equivalence first was Val, followed by Ser and Asp. Therefore, the three C-terminal residues could be identified as—DS V—OH. This suggests that the amino-acid designated (X) at the penultimate position 20 is a seine residue. Sequencing did not proceed beyond these three C-terminal amino-acid residues, suggesting a possible steric block to sequencing at the fourth residue designated (X) from the C-terminal end, at position 18. This could conceivably be due to the dinucleotide moiety attached covalently to the amino-acid at position 18.

Since from the phosphorus NMR spectrum, two phosphodiester signals not corresponding to a typical internucleotide 3' to 5'-phosphodiester linkage are indicated, it appears likely that the amino-acid at position 18 would have a hydroxyl group-containing side-chain; i.e. be either a serine, threonine, hydroxyproline or tyrosine residue, which is phosphorylated as a phosphodiester linkage. Since there are no threonine or hydroxyproline residue signals seen in the NMR spectra of Peptide-B, and the two tyrosine residues are accounted for at positions 13 and 14 from the N-terminal sequence position, this would indicate that a seine residue must be present at position 18. This would suggest the probable peptide sequence for a 21-amino-acid peptide with a probable covalent attachment of a dinucleotide at the hydroxyl group of the seine residue at position 18 to be:

```
            GEIPDAGGRIVDYYVGFSDSV
            1              18 21
``` or

```
        1          5              10              15
-NH2  Gly-Glu-Ile-Pro-Asp-Ala-Gly-Gly-Arg-Ile-Val-Asp-Tyr-Tyr-Val-Gly-Phe-Ser

20
Asp-Ser-Val-OH
```

This 21-amino-acid peptide segment would account for a molecular weight of 2216.4 Fragments consistent with this structure were observed in the mass spectra (see TABLE XI). The entire Peptide-B structure showed a MW of 2955 in mass spectral studies, indicating a MW 740 structure covalently attached to the peptide.

The NMR studies indicated two adenine units linked to each other through a 3' to 5'-phosphodiester linkage, as in RNA structure. A 2' to 5'-linkage is excluded because 2'-ribose carbon and hydrogen signals consistent with free 2' hydroxyl groups are observed for both adenine units. A diadenosine dinucleotide linked through a 3'-5' phosphodiester bond accounts for a fragment of MW 595. This leaves a molecular weight of 144 to be accounted for, which corresponds to two additional noninternucleotide phosphodiester linkages.

The diadenosine dinucleotide unit could be attached to the peptide serine hydroxyl group at either its 3' or 5' free hydroxyl group through the disphosphoester link. A 3'-link is indicated because a free 5'-hydroxyl group is observed (cross peak at 3.7 and 62.0 ppm in HSQC spectrum) for one of the adenine ribose units.

The presence of a free 5'-hydroxyl group in the adenosine dinucleotide structure was further indicated by the resistance of Peptide-B to hydrolysis by calf thymus alkaline phosphatase. This enzyme readily hydrolyses 5'-phosphate groups in DNA, RNA and nucleotides.

Figure 15:
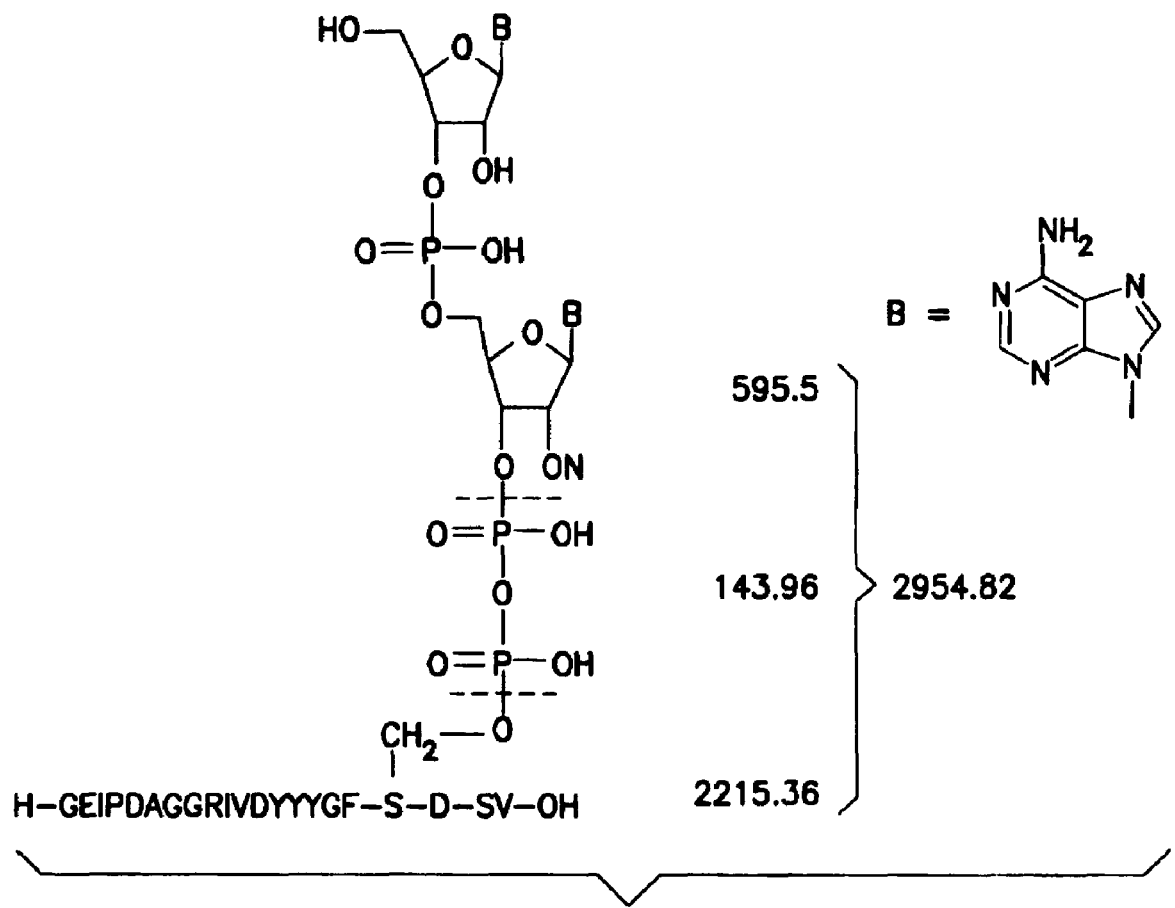
FIG. 15 shows the structure of Peptide-B.

The structure in FIG. 15 is consistent with the data acquired for Peptide-B in the structural studies, which is summarized as follows:

a. The structure is a 21 amino-acid long linear peptide covalently linked at the hydroxyl group of a serine residue at position 18 to a diadenosine dinucleotide unit through a diphosphodiester linkage at the 3'-position.

b. Mass spectral data are consistent with the assigned structure and with the N-terminal and C-terminal sequencing data. Mass fragments consistent with loss of the non-peptide dinucleotide adduct are observed, as well as sequential ion fragments confirming the assigned amino-acid sequence in the linear peptide moiety.

c. The three phosphorus diester linkages seen in the $^{31}$P-NMR spectrum can be explained by this structure, which includes one conventional internucleotide 3'-5' phosphodiester linkage and two signals resulting from a diphosphodiester linkage between a serine hydroxyl group on the peptide and a 3' hydroxyl group on the dinucleotide moiety.

Figure 16:
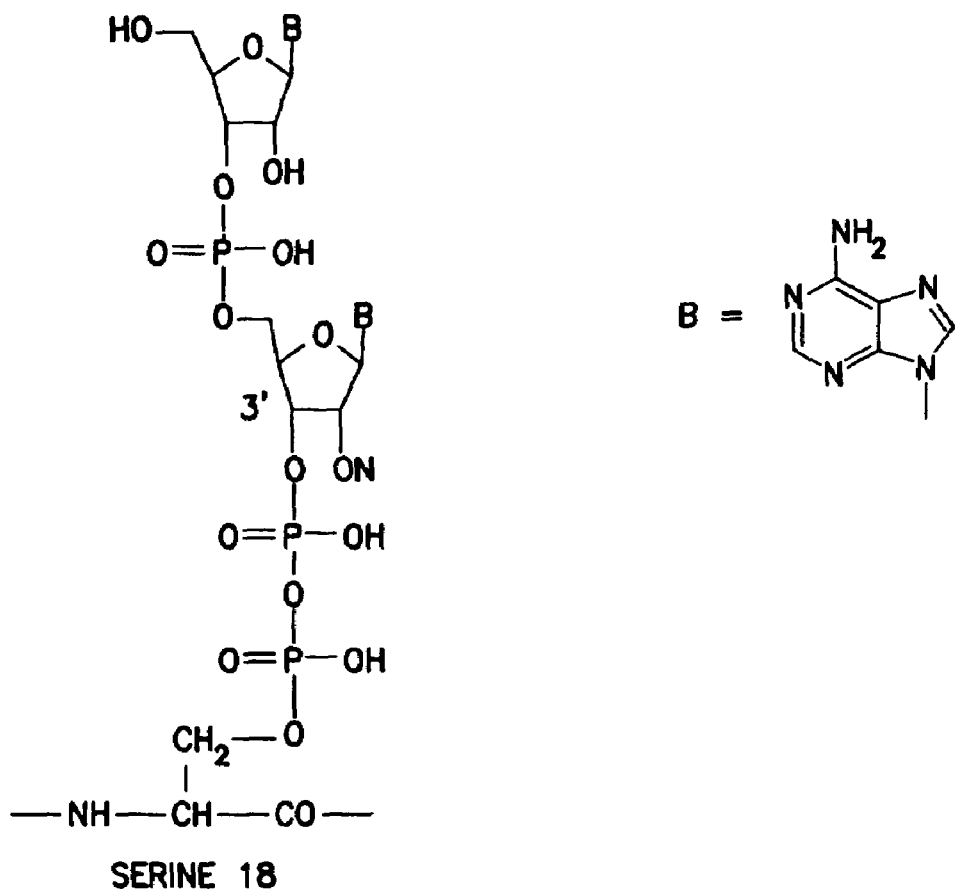
FIG. 16 shows the nature of the linkage between serine 18 and dinucleotide in Peptide-B.

FIG. 16 shows the nature of the linkage at the serine 18 via a diphosphodiester linkage to the diadenine dinucleotide unit.

Figure 17:
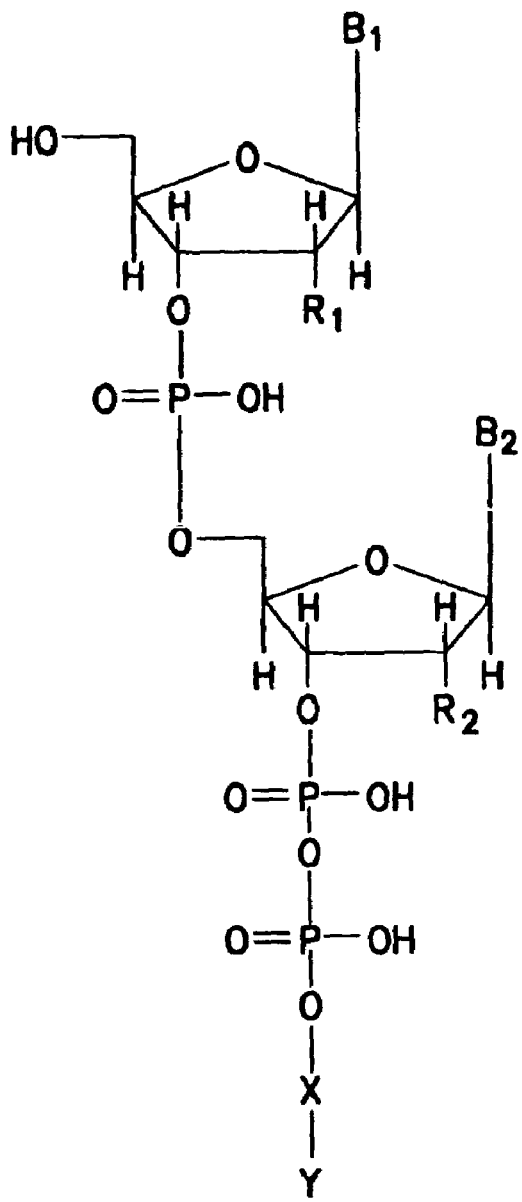
FIG. 17 shows the general structure of a peptide linked with a dinucleotides.

However, the present invention is not limited to the above described nucleotide-peptide structure. It is believed that the diphosphodiester linkage between the peptide and the oligonucleotide in the above described nucleotide-peptide structure is crucial to the activities of Product R. Thus, the present invention encompasses all other variations of the above structure that can be or should have been perceived by a person of ordinary skill in the art based on the above structure without departure from the present invention. FIG. 17 shows a general structure of the above described nucleotide-peptide, wherein B1 and B2 are purines or pyrimidines such as cytosine, guanine, adenine, thymine, uracil, 5-methylcytosine or 5-fluorouracil, R1 and R2 are hydrogen or hydroxyl group, X is a hydroxylated amino-acid residue such as residues of serine, threonine or tyrosine, and Y is the remaining portions of the peptide attached to the dinucleotide (peptide residues), exclusive of the hydroxylated amino-acid residue. The length of the peptide may vary but generally contains no more than 50 amino acids. At least one hydroxylated amino-acid residue is required in such peptide but the location of such residue may be anywhere along the peptide, including the N-terminal and C-terminal of the peptide.

Other amino acid residues in the peptide may be chosen from any known amino acids, and the dinucleotide may be ribodinucleotide or deoxyribonuycleotide.

Mass Spectral Studies on Peptide-B

Mass spectra were obtained on Peptide-B samples from Commonwealth Bioteclinologies, Inc., from Borealis Laboratories and from Louisiana State University. Both MALDI-TOF and electrospray techniques were used for these analyses. The table below (TABLE XI) shows the mass spectral fragment ions observed and the structural assignments.

TABLE XI

MASS SPECTRAL DATA FOR PEPTIDE-B

| Fragment | Mass Ion Expected | Mass Ion Observed |
| --- | --- | --- |
| /IVDYY/ | 654.74 | 655.7 |
| /DAGGRIV/ | 669.76 | 671.8 |
| /YYVGFS-28 | 689.79 | 688.8 |
| /IPDAGGRIV/ | 880.04 | 879.82 |
| /YYVGFSDS-H$_2$O | 901.95 | 901.97 |
| /PDAGGRIVDY/ | 1045.14 | 1044.18 |
|  |  | 1044.87 |
| /GGRIVDYYVG-28 | 1053.21 | 1053.1 |

TABLE XI-continued

MASS SPECTRAL DATA FOR PEPTIDE-B

| Fragment | Mass Ion Expected | Mass Ion Observed |
|---|---|---|
| GEIPDAGGRIV/ | 1066.20 | 1066.32 |
| /EIPDAGGRIVD-28 | 1096.23 | 1096.63 |
| /VDYYVGFSDS-H₂O | 1116.18 | 1118.34 |
| /EIPDAGGRIVD/ | 1124.24 | 1123.74 |
|  |  | 1123.90 |
| /AGGRIVDYYVG/ | 1151.58 | 1150.0 |
| /RIVDYYVGFS/ | 1201.37 | 1202.85 |
|  |  | 1202.82 |
| /GGRIVDYYVGF/ | 1228.40 | 1228.61 |
| /IVDYYVGFSDS-H₂O | 1229.34 | 1229.45 |
| /GGRIVDYYVGF-28 | 1230.41 | 1230.44 |
| /EIPDAGGRIVD/ | 1124.24 | 1123.74 |
| GEIPDAGGRIVD/ | 1181.30 | 1181.03 |
| /GGRIVDYYVGF/ | 1228.46 | 1229.12 |
|  |  | 1228.61 |
| /GGRIVDYYVGF-28 | 1200.39 | 1198.11 |
| /IPDAGGRIVDYY-28 | 1293.87 | 1293.87 |
| /IPDAGGRIVDYY-NH₃ | 1304.45 | 1302.00 |
| /PDAGGRIVDYYV/ | 1307.45 | 1308.42 |
| GEIPDAGGRIVDY/ | 1344.46 | 1342.09 |
|  |  | 1342.04 |
|  |  | 42.7 |
| /PDAGGRIVDYYVG-NH₃ | 1347.47 | 1346.77 |
| /PDAGGRIVDYYG/ | 1364.51 | 1364.02 |
|  |  | 1365.0 |
| /AGGRIVDYYVGFS/ | 1386.56 | 1386.02 |
| /IPDAGGRIVDYYV-28 | 1392.60 | 1391.12 |
| /GRIVDDYYVGFSDS | 1460.59 | 1459.63 |
|  |  | 1461.56 |
| /GRIVDDYYVGFSDS-H₂0 | 1441.68 | 1440.06 |
|  |  | 1440.41 |
| /IPDAGGRIVDYYVG/ | 1477.67 | 1475.01 |
| /DAGGRIVDYYVGFS-H₂O | 1483.63 | 1482.43 |
|  |  | 1482.45 |
| GEIPDAGGRIVDYY/ | 1507.63 | 1545.32(+K) |
| /EIPDAGGRIVDYV-NH₃ | 1532.70 | 1533.93 |
| /PDAGGRIVDYYVGF/ | 1511.68 | 1510.41 |
| /PDAGGRIVDYYVGFS-2NH3 | 1564.72 | 1565.6 |
|  |  | 1566.16 |
| /AGGRIVDYYVGFSD-H₂O | 1570.71 | 1569.89 |
| /AGGRIVDYYVGFSDS/ | 1588.72 | 1588.58 |
|  |  | 1587.01 |
|  |  | 1589.0 |
| /GEIPDAGGRIDYYV G-NH3 | 1589.76 | 1591.53 |
| GEIPDAGG RIVDYYV/ | 1606.76 | 1608.01 |
| /GEIPDAGGRIVDYYVG-28 | 1635.80 | 1635.82 |
| GEIPDAGGRIVDYYVG/ | 1663.81 | 1664.61 |
| /DAGGRIVDYYVGFSDS-28 | 1675.80 | 1675.95 |
|  |  | 1674.56 |
| /EIPDAGGRIVDYYVGF/ | 1753.96 | 1751.00 |
| GEIPDAGGRIVDYYVGF-NH3-28 | 1765.97 | 1765.6 |
| /PDAGGRIVDYYVGFSDS-28 | 1772.92 | 1772.92 |
| /AGGRIVDYYVGFSDSV-NH₃ | 1688.84 | 1688.69 |
| GEIPDAGGRIVDYYVGF/ | 1810.91 | 1890.61(+2K) |
| GEIPDACGRIVDYYVGFS/ | 1898.06 | 1898.61 |
| /EIPDAGGRIVDYYVGFSD/ | 1956.13 | 1957.64 |
| GEIPDAGGRIVDYYVGFSDS/ | 2100.28 | 2100.17 |
| GEIPDAGGRIVDYYVGFSDSV/ | 2199.35 | 2199.68 |
|  |  | 2200.17 |
|  |  | 2236.71(+K) |
|  |  | 2245.93/2246.10(+2Na) |
| GEIPDAGGRIVDYYVGFSDSV-NH₃ | 2181.35 | 2183.12 |
|  |  | 2183.68 |
| GEIPDAGGRIVDYYVGFSDSV•OH (M+) | 2216.29 | 2217.11 |
|  |  | 2217.18 |
|  |  | 2244.12(+K) |
|  |  | 2259.48(+2Na) |
|  |  | 2252.27(+2H2O) |
|  |  | 2262.24(+2Na) |
| M-Adenine, H₂0 | 2802.73 | 2803.09 |
| M-V(C-terminal) | 2857.86 | 2859.53 |
| M-(NH-V) (C-terminal) | 2842.85 | 2842.14 |
| M-Adenine | 2819.74 | 2821.70 |
| M-2H2O | 2918.81 | 2918.69 |
|  |  | 2940.33(+Na) |

TABLE XI-continued

MASS SPECTRAL DATA FOR PEPTIDE-B

| Fragment | Mass Ion Expected | Mass Ion Observed |
|---|---|---|
| M | 2954.82 | 2956.19 |
|  |  | 2994.99(+K) |
|  |  | 3000.63(+2Na) |

The mass spectral data supports the assigned structure of Peptide-B and also provides independent confirmation of the assignment of a glycine residue at position 16 and serine residues at positions 18 and 20 in the peptide structure by the fragments appearing at masses of 1664.61, 1898.61 and 2199.68 respectively.

Figure 18A:
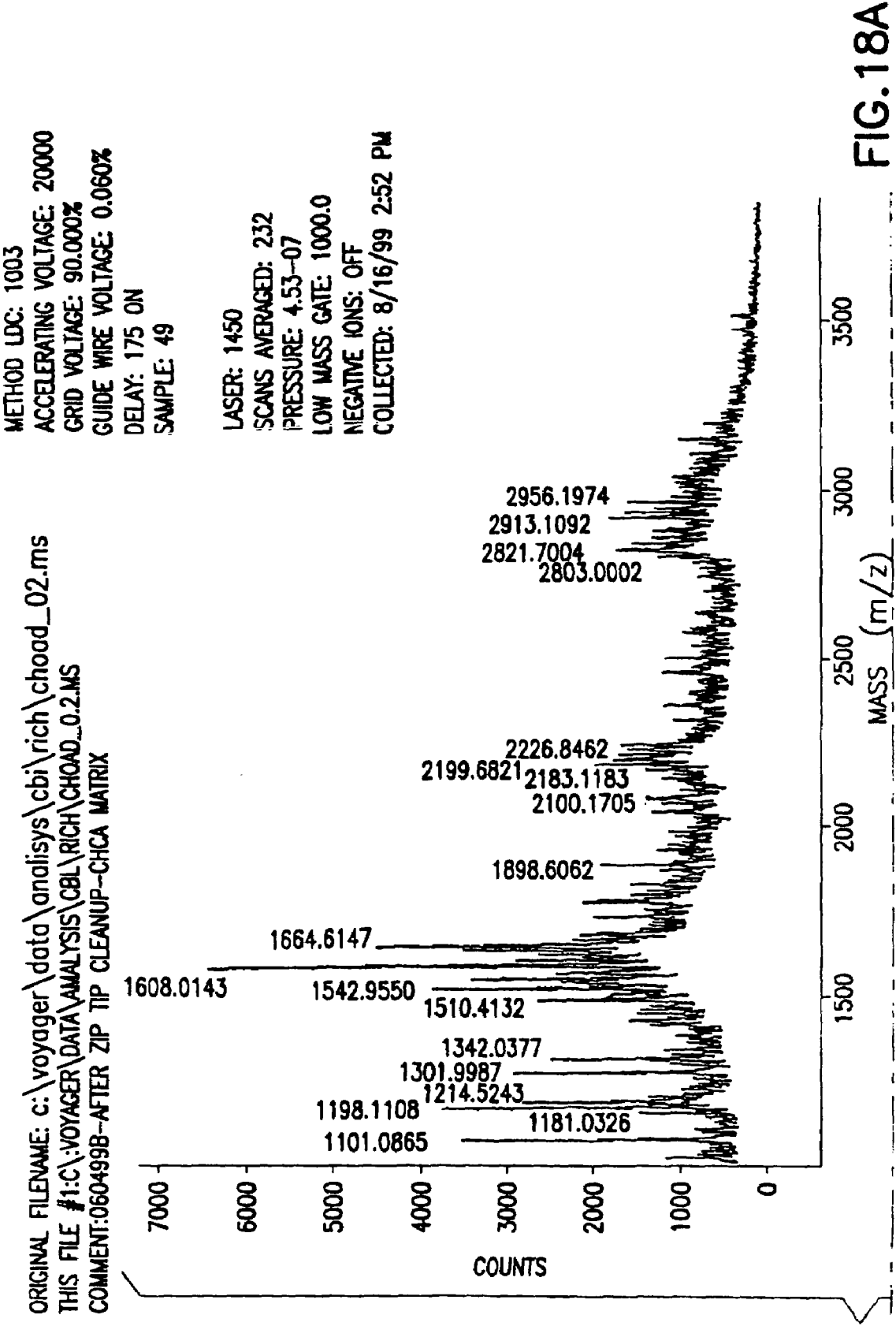
FIG. 18 is mass spectral data for Peptide-B.
Figure 18B:
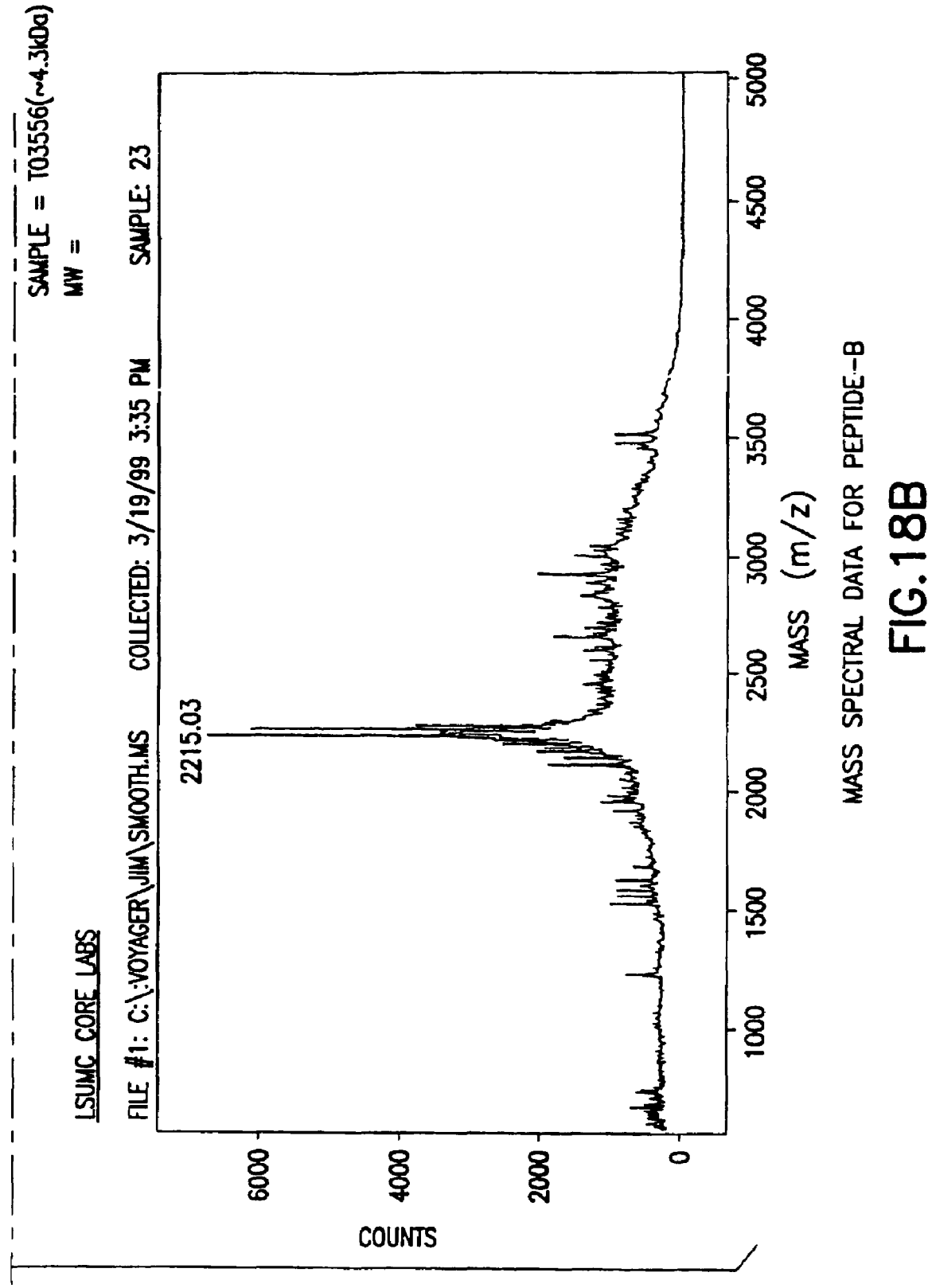

Representative mass spectra obtained on Peptide-B are shown in FIG. 18.

Peptide-B therefore consists of a 21-amino acid long straight-chain peptide covalently linked through the hydroxyl group of a seine residue at position 18 through a diphosphodiester group to the 3'-end of an adenylyl (3'-5') adenosine moiety. This makes Peptide-B a peptide-nucleic acid conjugate.

In sum, Product R was resolved into its constituent compounds, which were then identified by a series of structural chemical analyses. The process involved methodical gel-elution, HPLC analysis, SDS-gel electrophoresis, enzymatic studies, ultraviolet spectral analyses, NMR spectral analyses and mass spectroscopic analyses.

On the basis of these studies, it was concluded that the organic constituents of Product R are thirteen nucleoside/nucleotide compounds derived from the controlled hydrolysis of RNA, and two peptides.

The longer peptide, termed Peptide-A, with a MW of 3536 is a 31-amino acid fragment derived from bovine beta-casein. It has six spaced-out proline residues, which probably result in a tight folding of the peptide, accounting for its chemical stability and stability to enzymatic hydrolysis. It also has four basic glutamine residue in its structure.

The shorter peptide, a peptide-oligonucleotide conjugate termed Peptide-B, has a 21-amino-acid long chain attached at the seine residue in position 18 to a diadenine (3'-5') diribonucleotide through a diphosphodiester linkage at the 3'-position. This nucleopeptide conjugate has a MW 2215 peptide moiety attached to a 740 MW nonpeptidic adduct to give a total MW of 2955. The Peptide-B structure is hitherto undescribed in the scientific literature.

In addition, Product R contains sodium chloride as an inorganic ingredient, resulting from the neutralization of sodium hydroxide with hydrochloric acid during the manufacturing process.

There are therefore sixteen identified constituent compounds present in the Product R formulation—3 nucleosides, two nucleoside diphosphates and eight nucleoside monophosphates, together with two peptides (one of them a peptide-nucleic acid conjugate) and sodium chloride.

Biological activity of Product R peptide-A and peptide-B

U937 cells, a human pro-monocytic cell line obtained from a hystiocytic lymphoma grown under particular conditions have been shown to respond to Product R by increasing their production of interleukin-8 (IL-8) and monocyte chemotactic protein 1(MCP-1).

Commercially available quantitative ELISA assays are used to detect secretion of IL-S and MCP-1 by cultured U937 cells in response to the presence of Product R. A positive response in these assays is used as an indicator for biological activity of Product R. This test can also be used to demonstrate the biological activity of the purified peptide components of Product R.

Ammonium sulfate precipitation of Product R peptides: Product R samples are lyophilized and re-dissolved in 20% of original sample volume in water (5× concentrated). Ammonium sulfate crystals are added to the solution to reach 60% ammonium sulfate saturation (390 mg/ml solution), Gentle mixing solubilizes crystals. Protein precipitates appear after 30 mm to 1 hr incubation on ice and is centrifuged at 16,000 ×g for 30 min. at 40° C. The pellet is dissolved in 5% of original sample volume in water. The solution is desalted by gel filtration chromatography through a column of BioGel P-2. The column is eluted with 0.1× phosphate buffered saline (PBS). Only protein containing fractions are pooled and lyophilized.

Separation and isolation of two major peptides of Product R by gel chromatography: A BioGel P-1O column (1.6 cm×52 cm) was equilibrated with 0.1× concentration of PBS. Two ml of 2X concentrated Product R was applied to the column, which was eluted with the same buffer at a flow rate of 25 ml/hr. Four ml fractions were collected. All protein-containing fractions are analyzed by Sodium dodecyl sulfate polyacrylamide gel electrophoresis (SDS-PAGE). Fractions containing primarily peptide A and peptide B are pooled separately and lyophilized. Peptide A pool contains very little contamination of the other peptide, however, the peptide B pool is highly enriched but still contains peptide A as a major contaminant. A reasonable estimate of peptide purity in the pools is >90% for peptide A and >75% for peptide B.

U937 cell culture: The U937 human hystiocytic lymphoma cell line was purchased from the American Type Culture Collection. Cells were thawed and maintained in logarithmic growth (5-9×10$^5$ cells/mL) in RPMI 1640 culture medium, supplemented with 10% fetal bovine serum, heat inactivated at 56° C. for 30 min, 2mM L-glutamine and 1× Penicillin-Streptomycin.

Product R or isolated peptide treatment: Cells (1.0×10$^5$/ml) are cultured in growth medium containing Product R, isolated purified peptide solution, mixed peptides solution or Dulbecco's PBS for 2 days. Following centrifugation, the culture supernatants are analyzed using chemokine ELISA kits. Final concentration of Product R in the culture medium was 10% (v/v). The ammonium sulfate precipitated peptides were reconstituted in culture medium to yield a 10 mg/ml solution. Two 2-fold dilutions were prepared, also using culture medium as diluent. These solutions were used at a final concentration of 10% in the U937 cell culture. The individual lyophilized peptides were reconstituted in endotoxin-free water to yield 2 mg/ml solutions (which is the approximate concentration of each peptide in Product R). An equimolar mixture of both peptides was prepared at a final concentration of 4mg/ml. Both were used at a final concentration of 10% in the culture media for the assays.

Measurement of secreted IL-8 and MCP-1: The concentrations of IL-8 and MCP-1 in the culture supernatants are assayed by ELISA, using human IL-8 ELISA kits (Endogen. Inc.) and Quantikine human MCP-1 ELISA kits (R&D Systems, Inc.), respectively, according to manufacturer's instructions (with slight modifications for the MCP-1 ELISA). Each culture supernatant is assayed in triplicate. Absorbances are measured on a PowerWave 200 Microplate Scanning Spectrophotometer. Dilutions of the standard protein supplied by each manufacturer are utilized to generate a four-parameter logistic fit standard curve, and the concentration of chemokine in each supernatant is determined by extrapolation.

Figure 19:
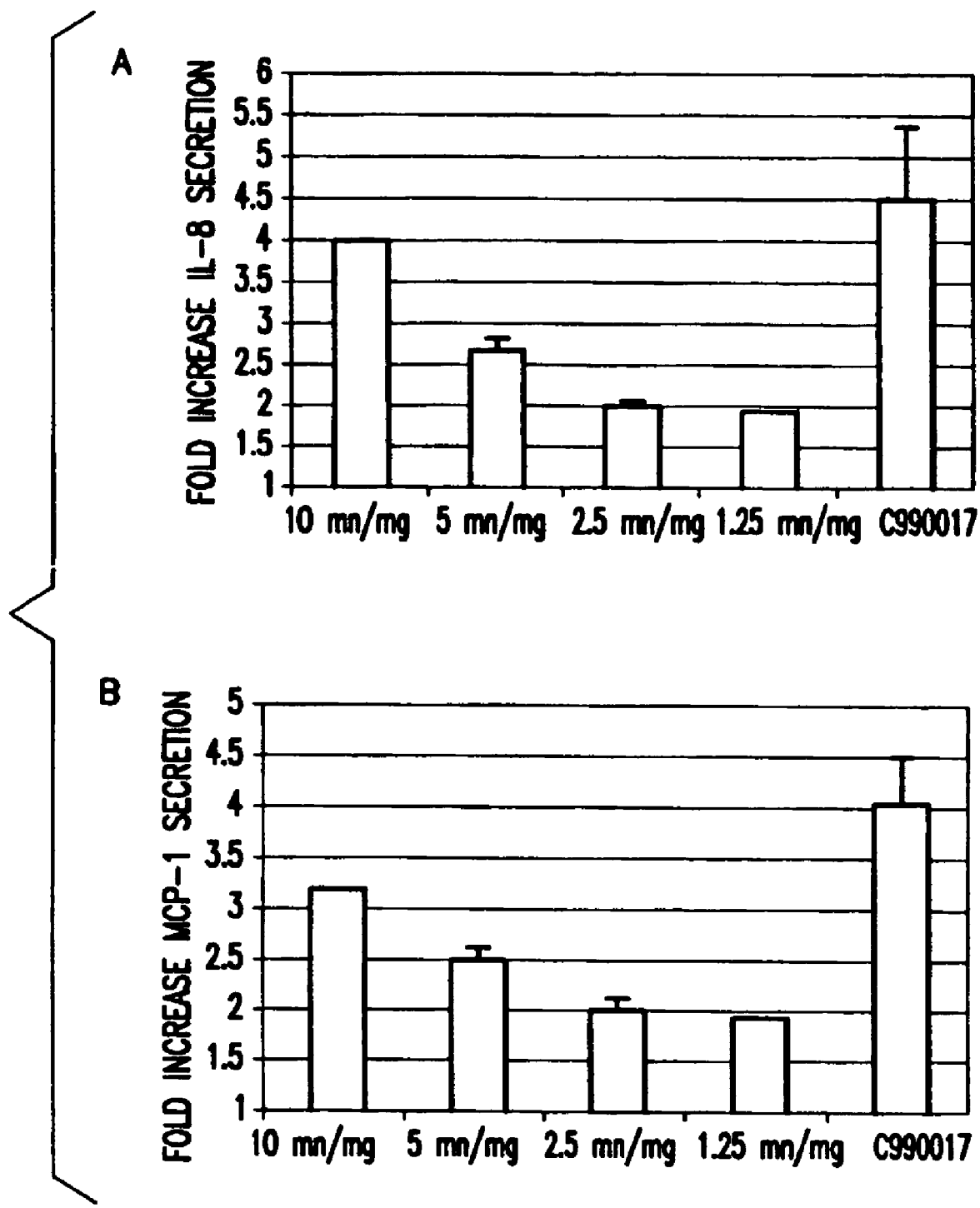
FIG. 19 shows the effect of Product R peptide component concentration on IL-8 and MCP-1 secretion by U937 cells. U937 cells ($1\times10^5$ cells) were cultured for 2 days in 2ml growth medium containing 10% of 10 mg/ml-1.25 mg/ml precipitated peptide solution or 10% Product R (Lot number C990017) or PBS. The chemokine concentrations in the supernatants were determined by ELISA. The fold increase over the basal level (secretion in the presence of PBS) was calculated by dividing the pg/ml values obtained with the peptide solutions or Product R by the pg/ml values obtained in the presence of PBS. Each bar represents the mean (±S.D.) of two independent experiments.

Results and conclusion: The peptide components of product R were isolated by ammonium sulfate precipitation, lyophilization and reconstitution in PBS. Their ability to increase secretion of IL-8 and MCP-1 by U937 cells was analyzed. Two different assays were performed with decreasing concentrations of the peptide solution, starting at 10 mg/ml. The average of the results for the two assays are shown in FIG. 19. For both IL-8 and MCP-1 secretion the response was dose dependent. For the IL-8 assay, 10% of a 10 mg/ml solution of the peptides was able to elicit a response similar to that of 10% complete Product R (same lot from which the peptides were precipitated). For MCP-1, 10% of a 10 mg/ml solution was not able to elicit a total response as compared to complete Product R.

Figure 20:
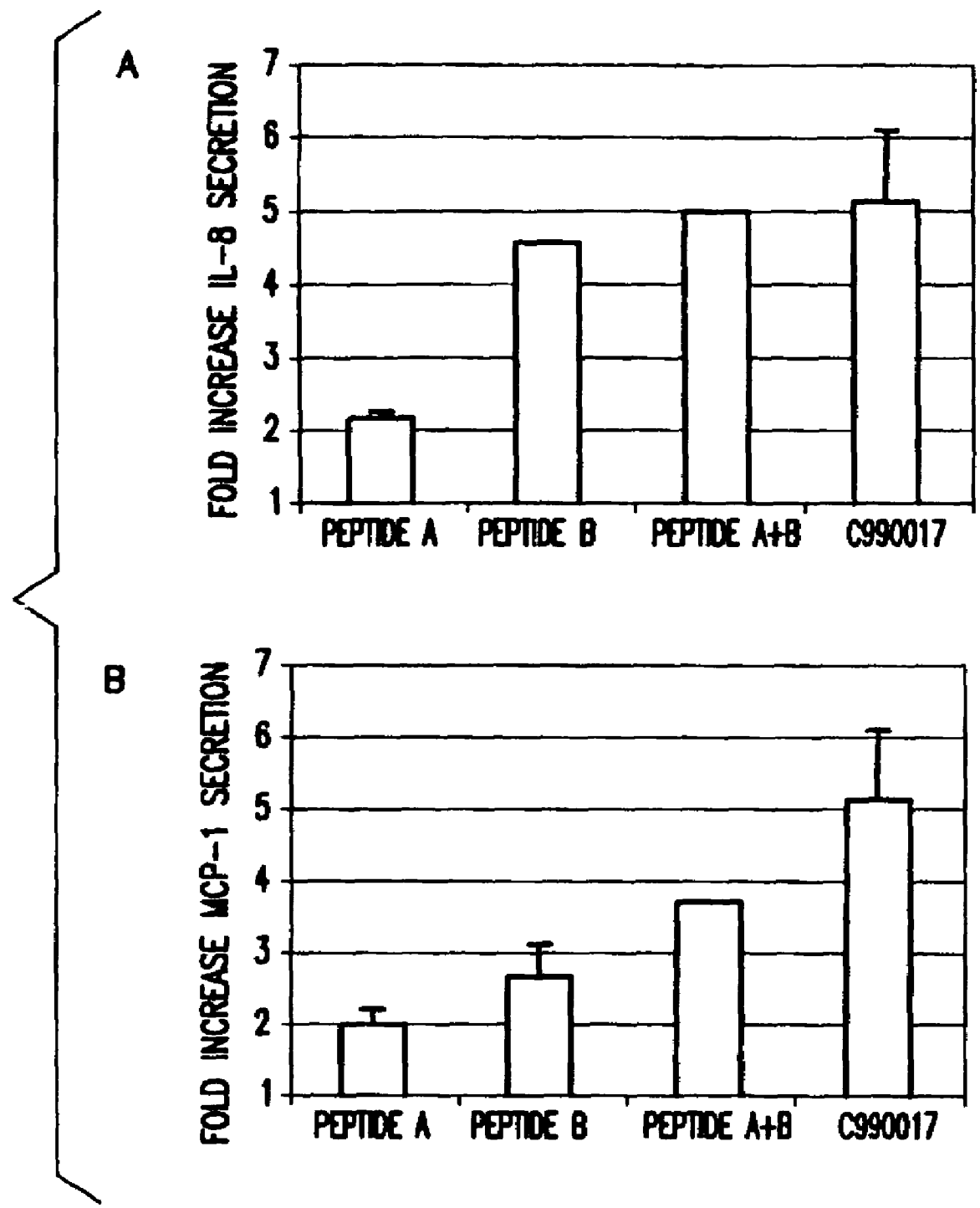
FIG. 20 shows the effect of Product R's isolated peptides A and B on IL-8 and MCP-1 secretion by U937 cells. U937 cells ($1\times10^5$ cells) were cultured for 2 days in 2 ml growth medium containing 10% of 2 mg/ml enriched solutions or the individual peptides or 4mg/ml mixed peptide solution. U937 cells were also cultured in the presence of 10% Product R (Lot number C990017) or PBS. The chemokine concentrations in the supernatants were determined by ELISA. The fold increase over the basal level (secretion in the presence of PBS) was calculated by dividing the pg/ml values obtained with the peptide solutions or Product R by the pg/ml values obtained in the presence of PBS. Each bar represents the mean (±S.D.) of two independent experiments.

To further analyze the ability of the peptide components of Product R to up-regulate the secretion of IL-8 and MCP-1 by U937 cells, enriched preparations in peptides A and B were prepared by gel filtration chromatography. Peptides A and B solutions (2 mg/ml) (preparation B was more contaminated with peptide A than vice versa) were assayed, both individually and mixed in equimolar amounts (4 mg/ml solution), at a final concentration of 10% in the culture media. Results for two independent assays are shown in FIG. 20. Peptide B solution maintained most of the ability of Product R to up-regulate IL-8 secretion by U937 cells, while peptide A solution only elicited a less response. The mixed peptide solution achieved the same activity as Product R. These results indicate the need for both peptides to be present in order to obtain full activity of Product R. In the case of MCP-1,each of peptide-A, peptide-B and the mixture of both failed to elicit a response same as that of Product R for MCP-1 up-regulation, suggesting the need for some other Product R component(s) for full Product R activity. The mixture of the two peptides was more active than each peptide individually, and peptide-B was slightly more active than peptide A, suggesting, again, the need for both peptides to be present for Product R's full activity. It is noted that in both occasions, peptide-B induces higher levels of secretion of IL-8 or MCP-1 than peptide-A. As peptide-B contains a dinucleotide covalently bound to the peptide, such structure may be responsible for the peptide-B's higher level of the biological activities.

The following example only serves as an illustration of the process of making Product R and should not be construed as a limitation of the present invention.

EXAMPLE

Suspend about 35.0 g of casein, about 17.1 g of beef peptone, about 22.0 g of nucleic acid (yeast RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs. pressure and 200-230° F. for a period of time until RNA is completely digested, for example, about 4 hours. At the end of the period, the autoclave is stopped and the reaction flask and contents are permitted to slowly cool to ambient temperature. Then cool for at least six hours at about 3-8° C. The resulting solution is filtered through 2 micron and 0.45 micron filters using inert gas such as nitrogen or argon at low pressure (1-6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165-210 mg/100 ml, the final volume is approximately 5 liters. The pH is then adjusted with either concentrated HCl (reagent grade ACS) or 1.0 normal NaOH to about 7.3-7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 14-16 pounds pressure for about 30 minutes. Following the sterilization cycle, the ampules with Product R are cooled and washed.

All quantities are subject to plus or minus 15% variation for pH, volume, and analytical adjustments.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A method for producing a therapeutic composition comprising the steps of:
   a) suspending about 35.0 grams of casein, about 17.1 grams of beef peptone, about 22.0 grams ribonucleic acid (RNA), and about 3.25 grams of bovine serum albumin in about 2.5 liters of water;
   b) adding about 16.5 grams of sodium hydroxide to the mixture from step a;
   c) autoclaving the product from step b at about 9 lbs pressure and 200-230° F. until the RNA is completely digested;
   d) cooling the product from step c to about 3-8° C.;
   e) sequentially filtering the product from step d through a 2 micron filter, a 0.45 micron filter and a 0.2 micron filter;
   f) diluting the product from step e with water to yield a final volume of about 5 liters;
   g) adjusting the pH of the product from step f to a range of about 7.3 to 7.6;
   h) filtering the product from step g through a second 0.2 micron filter; and
   i) autoclaving the product from step h at 240° F. and 20-30 pounds pressure for about 30 minutes;
   whereby the therapeutic composition comprises components having molecular weights less than 14 KDa.

2. The method of claim 1, wherein the RNA is yeast RNA.

3. The method of claim 1, wherein step e is repeated.

4. A product produced by the method of claim 1.

5. A product produced by the method of claim 2 or 3.

6. A pharmaceutical composition comprising a) the product of claim 4; and b) a pharmaceutically acceptable carrier.

* * * * *